(12) United States Patent
Callewaert et al.

(10) Patent No.: US 12,241,108 B2
(45) Date of Patent: Mar. 4, 2025

(54) GENETICALLY ENGINEERED EUKARYOTIC CELLS PRODUCING LACNAC-GLYCOPROTEINS

(71) Applicants: VIB VZW, Ghent (BE); UNIVERSITEIT GENT, Ghent (BE)

(72) Inventors: Nico Callewaert, Nevele (BE); Wander Van Breedam, Antwerp (BE); Francis Santens, Brussels (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 16/646,889

(22) PCT Filed: Sep. 13, 2018

(86) PCT No.: PCT/EP2018/074784
§ 371 (c)(1),
(2) Date: Mar. 12, 2020

(87) PCT Pub. No.: WO2019/053145
PCT Pub. Date: Mar. 21, 2019

(65) Prior Publication Data
US 2020/0255878 A1    Aug. 13, 2020

(30) Foreign Application Priority Data

Sep. 14, 2017 (GB) .................................. 1714764
May 9, 2018 (EP) .................................. 18171657

(51) Int. Cl.
*C12P 21/00* (2006.01)
*C12N 15/52* (2006.01)

(52) U.S. Cl.
CPC ............ *C12P 21/005* (2013.01); *C12N 15/52* (2013.01); *C12Y 204/01038* (2013.01)

(58) Field of Classification Search
CPC ............... C12P 21/005; C12P 21/00; C12Y 302/01096; C12Y 302/01035; C12Y 204/01038; C12N 9/2402; C12N 9/2474; C12N 2510/00; C12N 9/1051; C12N 9/2434

USPC ...... 435/252.3, 69.1, 320.1, 200, 74, 94, 96, 435/207, 193
See application file for complete search history.

(56) References Cited

FOREIGN PATENT DOCUMENTS

| WO | 2010015722 A1 | 2/2010 |
| WO | 2015032899 A1 | 3/2015 |
| WO | 2017005925 A1 | 1/2017 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Repnikova et al. ( J. of Neurosci 2010, 30, pp. 6466-6476.*
Meuris, L. et al. "GlycoDelete Engineering of Mammalian Cells Simplifies N-Glycosylation of Recombinant Proteins," Nature Biotechnology, vol. 32, No. 5, Apr. 20, 2014, pp. 485-489.
PCT International Search Report and Written Opinion; Application No. PCT/EP2018/074784 Applicant VIB VZW, International filing date of Sep. 13, 2018, date of mailing May 6, 2019, 23 pages.
Ueda, et al., "Chemoenzymatic Synthesis of Glycosylated Glucagon-like Peptide 1: Effect of Glycosylation on Propteolytic Resistance and in Vivo Blood Glucose-Lowering Activity," Journal of the American Chemical Society, vol. 131, No. 17, May 2009, pp. 6237-6245.

* cited by examiner

*Primary Examiner* — Robert B Mondesi
*Assistant Examiner* — Mohammad Y Meah
(74) *Attorney, Agent, or Firm* — Patent Law Works LLP

(57) ABSTRACT

The present invention provides means and methods for the production in eukaryotic cells of homogeneous forms of small glycan structures which carry terminal galactose residues. In addition, the invention provides glycan-conjugates based on specific coupling with galactose residues present on the recombinant glycoproteins.

Figure 1:
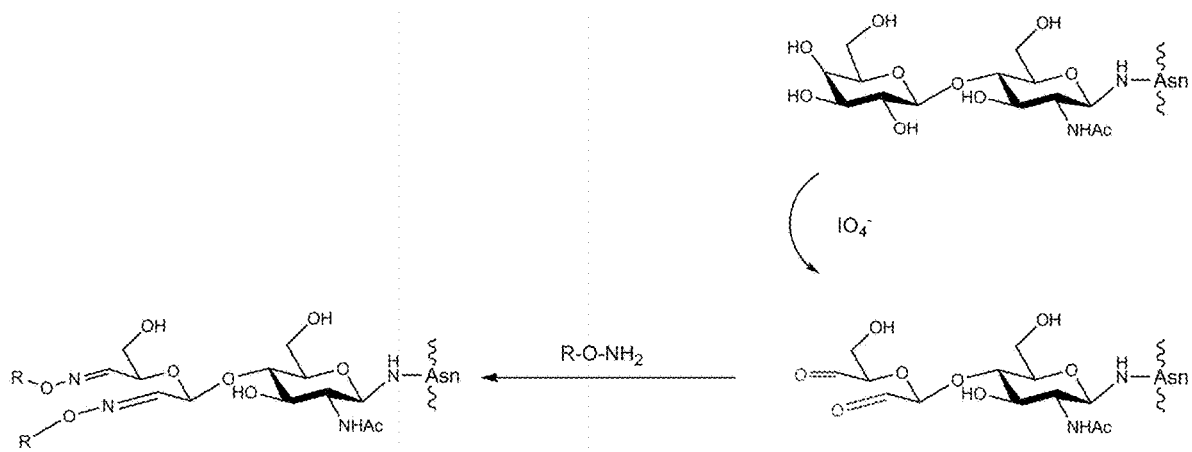

3 Claims, 9 Drawing Sheets
Specification includes a Sequence Listing.

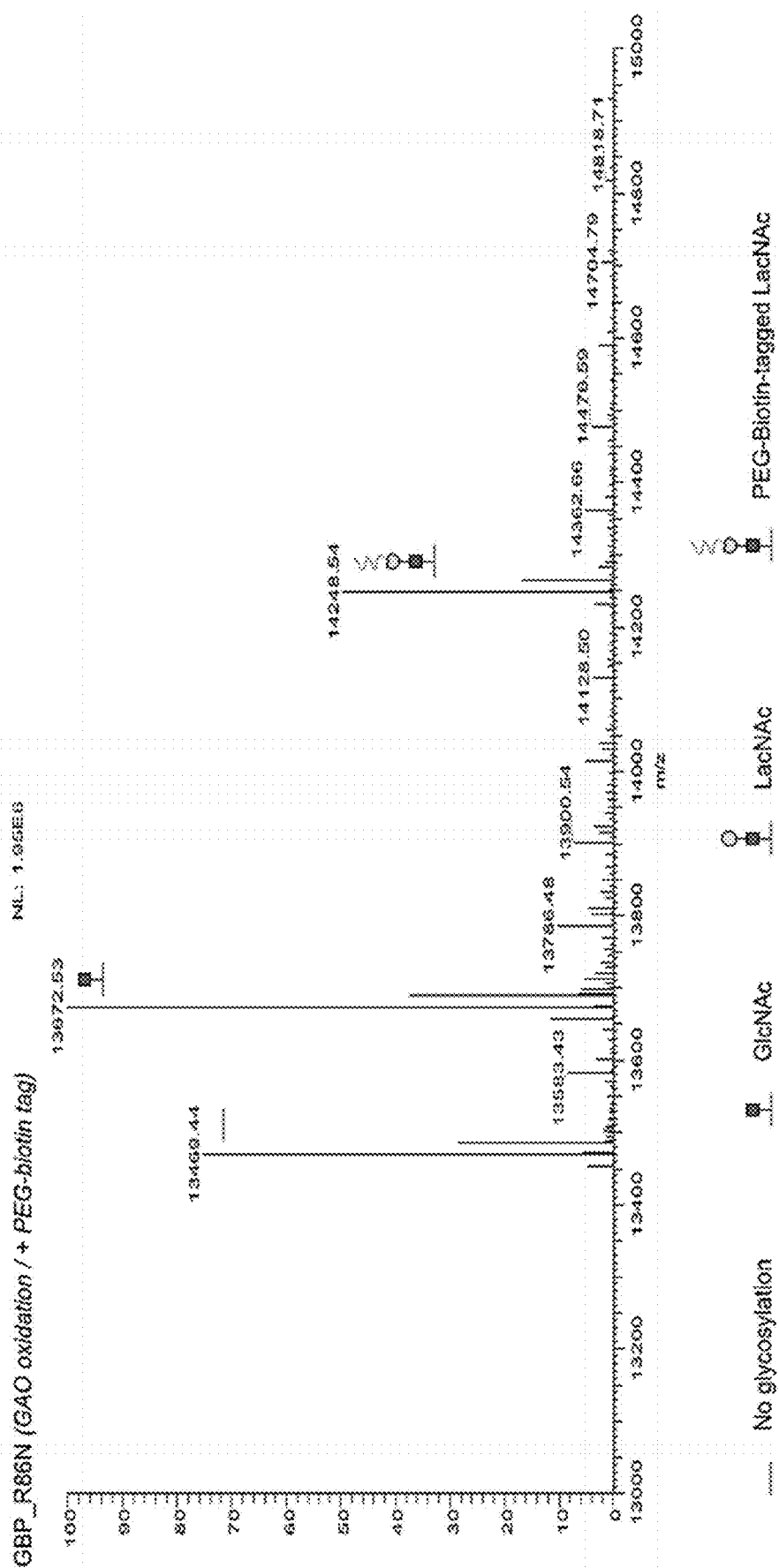

GENETICALLY ENGINEERED EUKARYOTIC CELLS PRODUCING LACNAC-GLYCOPROTEINS

FIELD OF THE INVENTION

The present application relates to the field of glycosylation, more particularly to the field of glycosylation engineering. Even more particularly the invention relates to the field of engineered eukaryotic cells which produce homogeneous forms of galactosylated glycans present on a recombinant glycoprotein. Accordingly, the present invention provides means and methods for the production in eukaryotic cells of homogeneous forms of small glycan structures which carry terminal galactose residues. In addition, the invention provides glycan-conjugates based on specific coupling with galactose residues present on the recombinant glycoproteins.

INTRODUCTION TO THE INVENTION

Therapeutic proteins play an increasingly important role in the pharmaceutical industry, achieving annual total sales of ~$48 billion in 2009 (Aggarwal (2010) *Nat. Biotechn.*, 28 (11), 1165-71). Unlike in the past, therapeutic proteins are now administered to patients with a whole variety of disease conditions, sometimes in high milligram quantities per dose. They represent an integrated part of treatment for various cancer types, autoimmune diseases, and replacement therapies such as enzyme and hormone substitutes. Among the biggest blockbusters in the biopharmaceutical industry are therapeutic proteins like Erythropoietin (EPO, Epogen®; Amgen), and the chimeric IgG1 monoclonal antibody Infliximab (Remicade®; Centocor Ortho Biotech Inc.) with annual sale volumes of $2.6 and $3.2 billion each in 2009, respectively (Aggarwal (2010) *Nat. Biotechn.*, 28 (11), 1165-71). The vast majority of therapeutic proteins require posttranslational modification with N-glycans and less frequently, O-glycans. Glycosylation is a very critical modification of therapeutic proteins, known to significantly modulate yield, bioactivity, solubility, stability against proteolysis, immunogenicity, and clearance rate from circulation. Depending on the source, the glycosylation pattern of the recombinant protein product varies greatly: starting with bacterial systems that generally do not glycosylate, followed by yeast, plants and insect cell systems generating glycan types that are absent in humans and can be immunogenic, to mammalian systems with human-like complex glycans.

Significant progress has been made over the past decade to overcome the current limitations of non-mammalian expression systems by glycoengineering approaches to achieve expression of human-like glycosylation patterns but currently, the vast majority of therapeutic glycoproteins is produced by mammalian production platforms with their natural ability to express human-like glycosylation. Both natural and recombinant glycoproteins are typically produced as a mixture of glycoforms that differ only in the structure of the pendent oligosaccharides.

Glycoproteins with sialic acid as terminal and thus most exposed monosaccharide were reported to make up the largest part of the glycoproteins (Schauer, R., Glycoconj J. 2000 July-September; 17(7-9)). Next to this fraction, glycoproteins presenting free galactose residues are present which are bound by asialo-glycoprotein receptors of the liver and consequently removed from serum (Morell, A. G. et al., J Biol Chem. 1971 Mar. 10; 246(5)).

Conjugates based on the coupling of specific moieties to therapeutic glycoproteins are being used in the pharmaceutical industry for increasing the half-life of glycoproteins, for coupling of glycoproteins to toxic pay loads, to detection agents and to targeting moieties. Conjugates produced via glycan coupling are particularly desired to prevent a-specific linkage to amino acids. Glycoproteins having glycans with terminal galactose residues are particularly useful for glycan-specific coupling. For example, galactose can be selectively oxidized at the C6 position using Galactose Oxidase (GAO), yielding a free aldehyde group which can subsequently form an oxime by reaction with a aminooxy-containing molecule. To efficiently employ the coupling to galactose residues a high and homogeneous degree of terminal galactosylated glycans is desired to ensure homogeneity of glycoprotein conjugates. Thus, it would be particularly useful to develop technologies allowing for an enhanced and homogeneous galactosylation of glycoproteins which can be directly produced in a eukaryotic host.

Although a variety of cell culture systems exist (e.g. yeast cells, insect cells, mammalian cells, plant cells) which can be used for the production of therapeutic glycoproteins in commercially feasible quantities, in practice a desired glycosylation pattern on a recombinantly produced protein is difficult to achieve and is unpredictable. Indeed, although N-glycans originate from a common dolichol-structure different host cells (e.g. mammalian, insect, yeast, fungal, plant or prokaryotic cell culture systems) typically a large variety of structures is formed due to a combinatorial use of different precursor monosaccharides, glycosyltransferase and linkage-types (Bork, K. et al., J Pharm Sci. 2009 October; 98(10)) inherently specific for each production host.

We previously established a new cellular glycosylation platform (cells having a GlycoDelete background) for the production of glycoproteins modified with more homogeneous glycans (see WO2010015722 and WO2015032899). Mammalian cells with a GlycoDelete background produce glycoproteins comprising a mixture of N-glycans consisting of GlcNAc residues, consisting of GlcNAc modified with galactose (LacNAc) residues and consisting of sialyl-LacNAc residues while yeast cells with a GlycoDelete background produce glycoproteins comprising N-glycans consisting of only GlcNAc residues. As heterogeneity in glycosylation does not only originate from N-linked sugars, but also from O-glycans attached to the glycoprotein, it can be desirable to remove these diverse carbohydrate chains from the polypeptides of the invention.

This can be achieved by expressing an endoglucosaminidase enzyme in a cell that is deficient in expression and/or activity of an endogenous UDP-Galactose 4-epimerase (GalE) as described in WO2017005925. Cells described in the latter application are also particularly envisaged as glyco-engineered cells according to the present invention and herein further described as GlycoDoubleDelete cells or cells having a GlycoDoubleDelete background.

For conjugation purposes, it can be advantageous to have glycans with a terminal galactose residue like the LacNAc glycan. Galactose can be specifically oxidized using GAO to allow subsequent conjugation via oxime ligation or other chemistries. Alternatively, sialyltransferases can be used to modify the galactose with Azido-Sialic acid, the azido-group of which can subsequently be used for conjugation via click chemistry. We therefore investigated whether eukaryotic cells having a GlycoDelete background or eukaryotic cells having a GlycoDoubleDelete background could be adapted for producing glycoproteins comprising N-glycans consisting of LacNAc structures.

SUMMARY OF THE INVENTION

In the present invention we surprisingly found that higher eukaryotic cells engineered to have a GlycoDelete background, and which are not capable of producing detectable amounts of N-glycans which comprise terminal sialic acid residues, produce recombinant proteins with homogeneous amounts of N-glycans consisting predominantly of LacNAc. In addition, we showed that lower eukaryotic cells, having a GlycoDelete background, and having an exogenously introduced beta-1,4-galactosyltransferase, produce recombinant proteins with homogeneous amounts of N-glycans consisting of LacNAc.

Accordingly, the present invention provides in a first aspect a eukaryotic cell lacking the capacity to synthesize N-glycans which comprise sialic acid on glycoproteins comprising:
  a first exogenous nucleic acid sequence encoding an endoglucosaminidase enzyme, and
  a second exogenous nucleic acid sequence encoding a glycoprotein.

In a further aspect the present invention provides a eukaryotic cell lacking glycoproteins comprising N-glycans which comprise sialic acid residues comprising:
  a first exogenous nucleic acid sequence encoding an endoglucosaminidase enzyme, and
  a second exogenous nucleic acid sequence encoding a glycoprotein.

In a further aspect the present invention provides a eukaryotic cell, which has less than 5%, preferably less than 1% N-glycans comprising sialic acid residues, said eukaryotic cell comprises:
  a first exogenous nucleic acid sequence encoding an endoglucosaminidase enzyme, and
  a second exogenous nucleic acid sequence encoding a glycoprotein.

The present invention provides in a further aspect a eukaryotic cell lacking UDP-N-acetylglucosamine-2-epimerase/N-acetylmannosamine kinase enzymatic activity comprising:
  a first exogenous nucleic acid sequence encoding an endoglucosaminidase enzyme,
  a second exogenous nucleic acid sequence encoding a glycoprotein,
  and optionally third exogenous nucleic acid sequence encoding a beta-1,4-galactosyltransferase.

In a further aspect the present invention provides a eukaryotic cell lacking detectable amounts of glycoforms of glycoproteins comprising N-glycans comprising sialic acid residues and lacking UDP-Glc-4-epimerase activity comprising:
  a first exogenous nucleic acid sequence encoding an endoglucosaminidase enzyme,
  a second exogenous nucleic acid sequence encoding a glycoprotein,
  optionally a third exogenous nucleic acid sequence encoding a beta-1,4-galactosyltransferase In a further aspect the present invention provides a eukaryotic cell lacking glycoforms of glycoproteins comprising N-glycans comprising sialic acid residues, said eukaryotic cell comprising:
  a first exogenous nucleic acid sequence encoding an endoglucosaminidase enzyme,
  a second exogenous nucleic acid sequence encoding a glycoprotein,
  optionally a third exogenous nucleic acid sequence encoding a beta-1,4-galactosyltransferase
  optionally a fourth exogenous nucleic acid sequence encoding an UDP-Glc-4-epimerase.

In a further aspect the present invention provides a eukaryotic cell lacking glycoforms of glycoproteins comprising N-glycans comprising sialic acid residues and also lacking ER-mannosidase I and/or glucosidase I and/or glucosidase II and/or N-acetylglucosaminyl transferase I and/or N-acetylglucosaminyl transferase II and/or mannosidase II enzymatic activity comprising:
  a first exogenous nucleic acid sequence encoding an endoglucosaminidase enzyme,
  a second exogenous nucleic acid sequence encoding a glycoprotein,
  optionally a third exogenous nucleic acid sequence encoding a beta-1,4-galactosyltransferase
  optionally a fourth exogenous nucleic acid sequence encoding an UDP-Glc-4-epimerase and
  optionally a fifth exogenous nucleic acid sequence encoding an UDP-galactose transporter.

In a further aspect the present invention provides a eukaryotic cell lacking glycoforms of glycoproteins comprising N-glycans comprising sialic acid residues and also lacking ER-mannosidase I and/or glucosidase I and/or glucosidase II and/or N-acetylglucosaminyl transferase I and/or N-acetylglucosaminyl transferase II and/or mannosidase II enzymatic activity comprising:
  a first exogenous nucleic acid sequence encoding an endoglucosaminidase enzyme,
  a second exogenous nucleic acid sequence encoding a glycoprotein,
  optionally a third exogenous nucleic acid sequence encoding a beta-1,4-galactosyltransferase and
  optionally a fourth exogenous nucleic acid sequence encoding an UDP-galactose transporter.

In a further aspect the endoglucosaminidase enzyme and/or the beta-1,4-galactosyltransferase and/or the UDP-galactose transporter are operably linked to an ER or Golgi localization signal.

In a further aspect the endoglucosaminidase enzyme is operably linked to a secretion signal.

In a sixth aspect the eukaryotic cell is a lower eukaryotic cell such as the yeasts *Pichia pastoris* or *Saccharomyces cerevisiae* or a fungal cell such as *Aspergillus*.

In a further aspect the eukaryotic cell is a higher eukaryotic cell such as a mammalian cell or a plant cell.

In a further aspect the eukaryotic cells are used to produce a glycoprotein.

In a further aspect the invention provides a composition comprising a plurality of glycoforms of a recombinant glycoprotein, wherein the N-glycans present on said glycoforms comprise N-glycans consisting of GlcNAc residues and N-glycans consisting of LacNAc residues and wherein the ratio of N-glycans consisting of LacNAc residues over the sum of the N-glycans consisting of GlcNAc residues and N-glycans consisting of LacNAc residues, is at least 80%.

In a further aspect the invention provides a composition comprising a plurality of glycoforms of a recombinant glycoprotein, wherein the N-glycans present on said glycoforms comprise N-glycans consisting of GlcNAc residues and N-glycans consisting of LacNAc disaccharides and said glycoforms do not comprise detectable levels of N-glycans consisting of Sialyl-LacNAc trisaccharides and wherein the amount of N-glycans consisting of LacNAc disaccharides over the sum of the N-glycans consisting of GlcNAc residues and N-glycans consisting of LacNAc disaccharides, is at least 80%, is at least 85% or is at least 90%.

In a further aspect the invention provides a composition comprising a plurality of glycosylated forms of a recombinant glycoprotein, wherein glycosylated forms comprising N-glycans consisting of GlcNAc residues and other glycosylated forms comprising N-glycans consisting of LacNAc residues are present in said composition and wherein the amount of N-glycans consisting of LacNAc residues is at least 80%, is at least 85% or is at least 90% in the pool of N-glycans consisting of GlcNAc residues and N-glycans consisting of LacNAc residues of said recombinant glycoprotein.

In another aspect the invention provides a composition comprising a plurality of glycosylated forms of a recombinant glycoprotein, wherein glycosylated forms comprising N-glycans consisting of GlcNAc residues and other glycosylated forms comprising N-glycans consisting of LacNAc residues are present in said composition and wherein the amount of glycosylated forms comprising N-glycans consisting of LacNAc residues is at least 80%, is at least 85% or is at least 90% in the pool of glycosylated forms comprising N-glycans consisting of GlcNAc residues and glycosylated forms comprising N-glycans consisting of LacNAc residues of said recombinant glycoprotein.

In another aspect the invention provides a composition comprising a plurality of glycosylated forms of a recombinant glycoprotein, which glycoprotein has one N-glycosylation site, and wherein glycosylated forms comprising N-glycans consisting of GlcNAc residues and other glycosylated forms comprising N-glycans consisting of LacNAc residues are present in said composition and wherein the amount of glycosylated forms comprising N-glycans consisting of LacNAc residues is at least 80%, is at least 85% or is at least 90% in the pool of glycosylated forms comprising N-glycans consisting of GlcNAc residues and glycosylated forms comprising N-glycans consisting of LacNAc residues of said recombinant glycoprotein.

In a further aspect the recombinant glycoprotein is a growth factor, an antibody, an Fc containing molecule (or an Fc-fusion protein), a single domain antibody, an antibody fragment, a vaccine, a regulatory protein, a cytokine, a membrane protein, an antigen, a receptor, VHH or a glycoprotein having one or more artificially introduced N-glycosylation sites.

In a further aspect the invention provides a composition comprising a conjugate between a glycoprotein comprising a N-glycan consisting of a LacNAc disaccharide present in a composition as herein defined above and a conjugated moiety connected to said LacNAc dissacharide.

In a further aspect the invention provides a composition as herein defined above for the production of a conjugate wherein the conjugated moiety is connected to the N-glycan consisting of a LacNAc disaccharide present on a recombinant glycoprotein.

In a further aspect the invention provides a composition as herein defined above for use as a medicament.

In a further aspect the invention provides a pharmaceutical composition comprising a composition as herein defined above.

In a further aspect the invention provides a conjugate as herein defined above for use as a medicament.

In a further aspect the invention provides a pharmaceutical composition comprising a conjugate as herein defined above.

FIGURES

FIG. 1: The vicinal diol in Galactose, the terminal residue of the LacNAc (GlcNAc-Gal) GlycoDelete N-glycan, can be selectively oxidized using periodate, yielding free aldehyde groups. These free aldehydes can react with aminooxy-containing molecules to form stable oxime bonds. R is a molecule of interest, such as a PEG chain or toxin.

Figure 2:
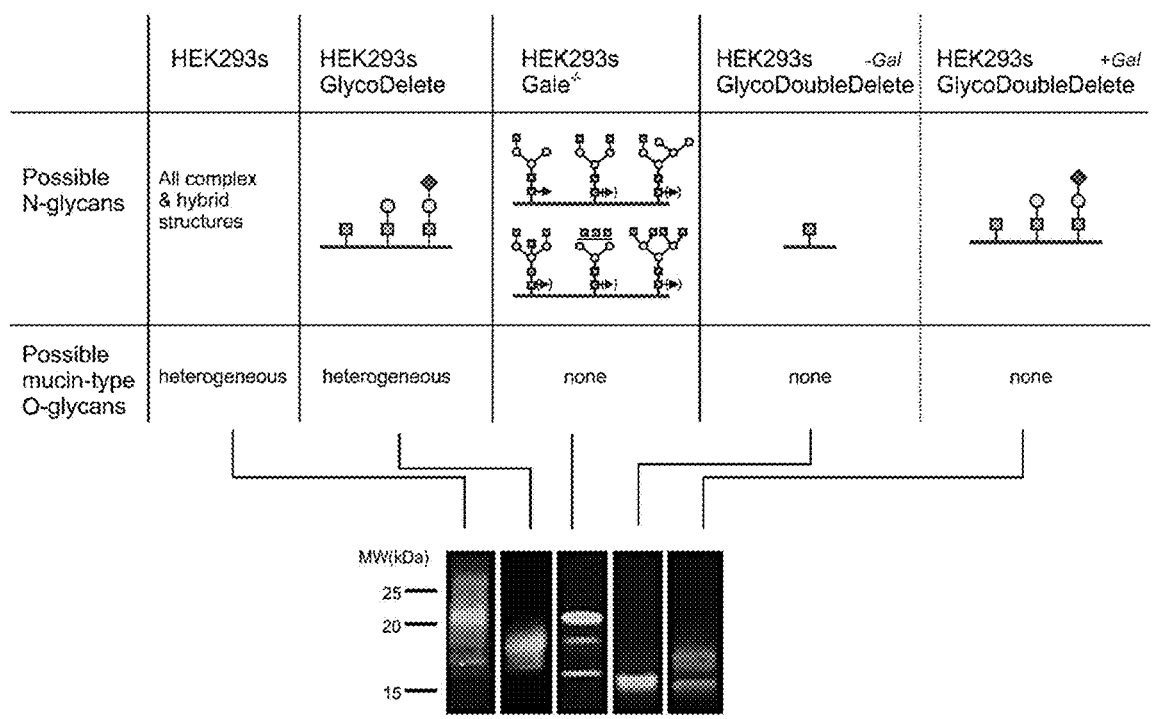

FIG. 2: Glycoengeneering of the HEK293s cell line. First column: wild type HEK293s produces all complex and hybrid N-glycan structures and heterogeneous mucin-type O-glycan structures, Second column: HEK293s cell line with GlycoDelete background produces N-glycans consisting of GlcNAc, LacNAc and sialyl-LacNAc and heterogenous mucin-type O-glycans, third column: HEK293s cells which are deficient in GalE produce complex N-glycan structures and no mucin-type O-glycans, fourth column: HEK293s cells having a GlycoDoubleDelete background with no galactose in the medium produce N-glycans with only GlcNAc and no mucin-type O-glycans, fifth column: HEK293s cells having a GlycoDoubleDelete background with galactose supplemented in the medium produce N-glycans with GlcNAc, LacNAc and sialyl-LacNAc and no mucin-type O-glycans.

Figure 3A:
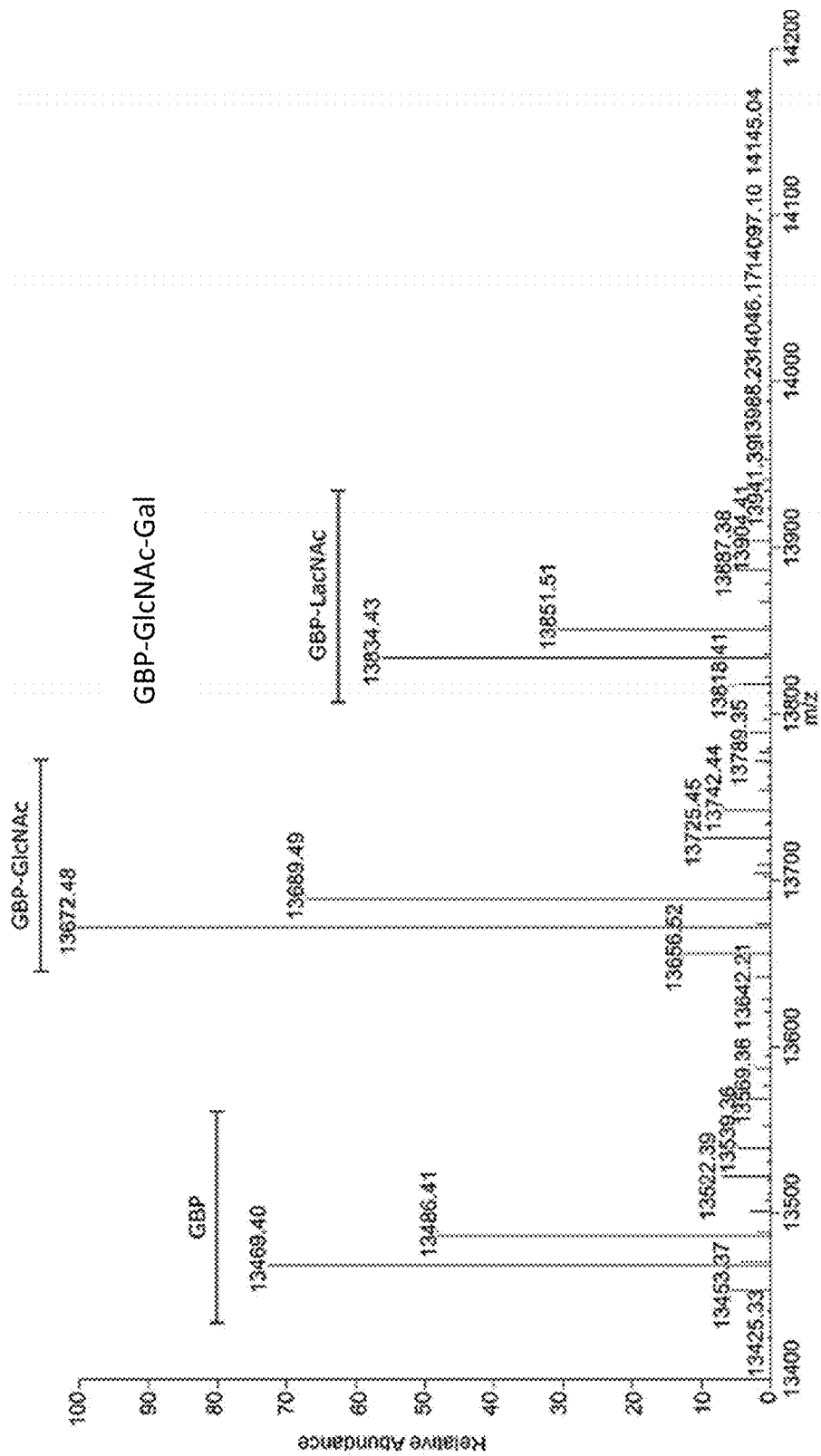
Figure 3B:
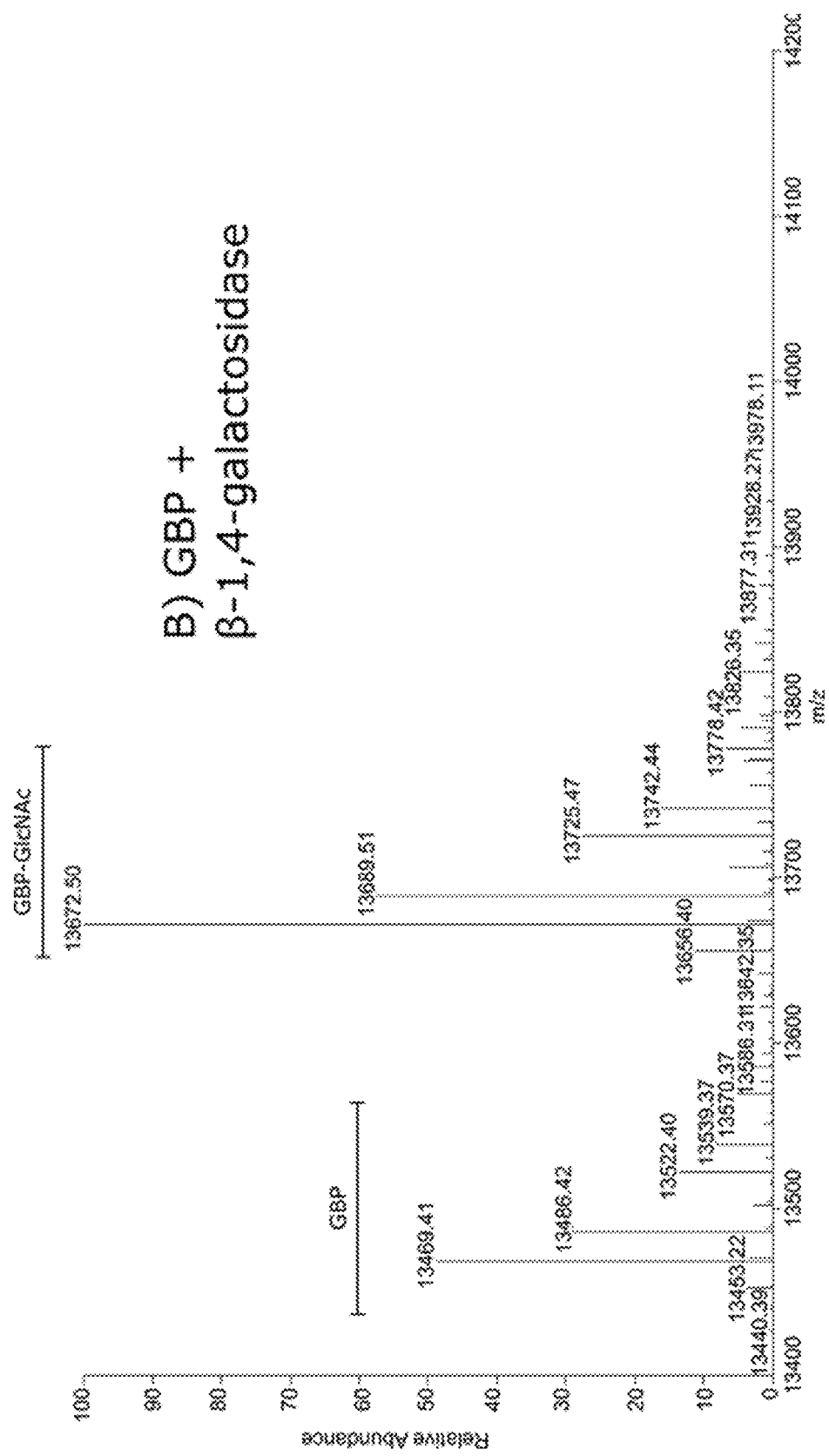

FIGS. 3A and 3B: FIG. 3A shows the intact mass spectrum of purified GBP_R86N produced in *Pichia* GlycoDelete LacNAc cells. "GBP": Unglycosylated nanobody GBP_R86N, "GBP-GlcNAc": GBP_R86N modified with a single GlcNAc glycan, "GBP-GlcNAc-Gal": GBP_R86N modified with a GlcNAc-Gal (LacNAc) glycan. FIG. 3B shows the mass spectrum of purified GBP_R86N produced in *Pichia* GlycoDelete LacNAc cells after treatment with *S. pneumoniae* β-1,4-galactosidase.

Figure 4:
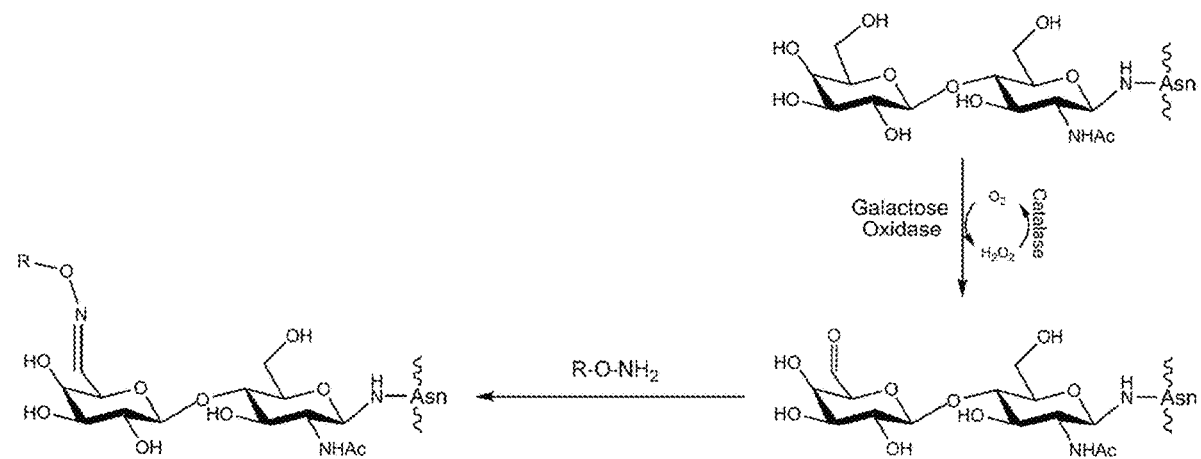

FIG. 4: Chemoenzymatic conjugation strategy. The C6 hydroxyl group of Galactose, the terminal residue of the LacNAc GlycoDelete N-glycan, is selectively oxidized using Galactose Oxidase (GAO), yielding a free aldehyde group. This free aldehyde can react with aminooxy-containing molecules to form stable oxime bonds. R is a molecule of interest, such as a PEG chain or toxin.

Figure 5:
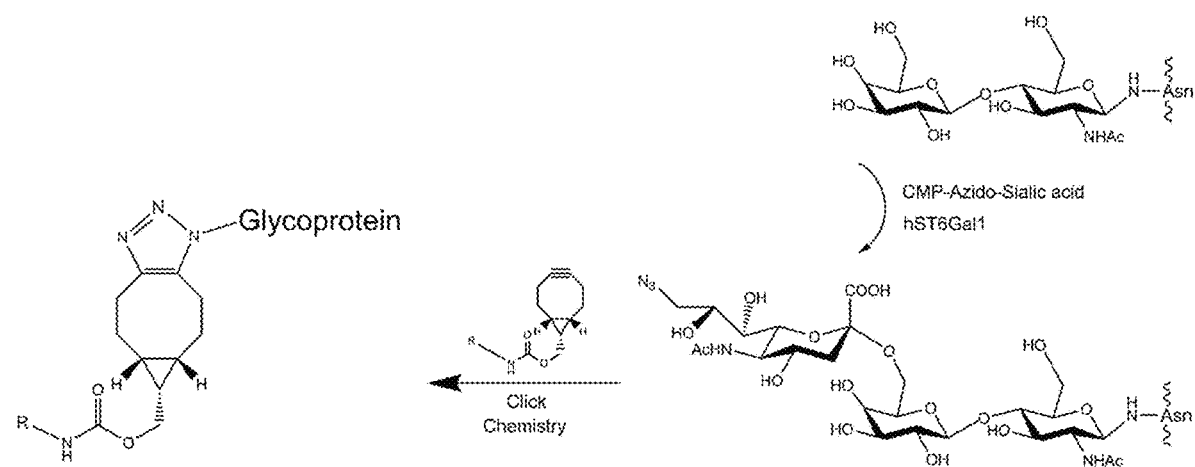

FIG. 5: Schematic outline for chemo-enzymatic coupling of an azide-modified form of Sia (AzSia) to a LacNAc N-glycan, followed by a click chemistry reaction of the azide with a strained alkyne.

Figure 6A:
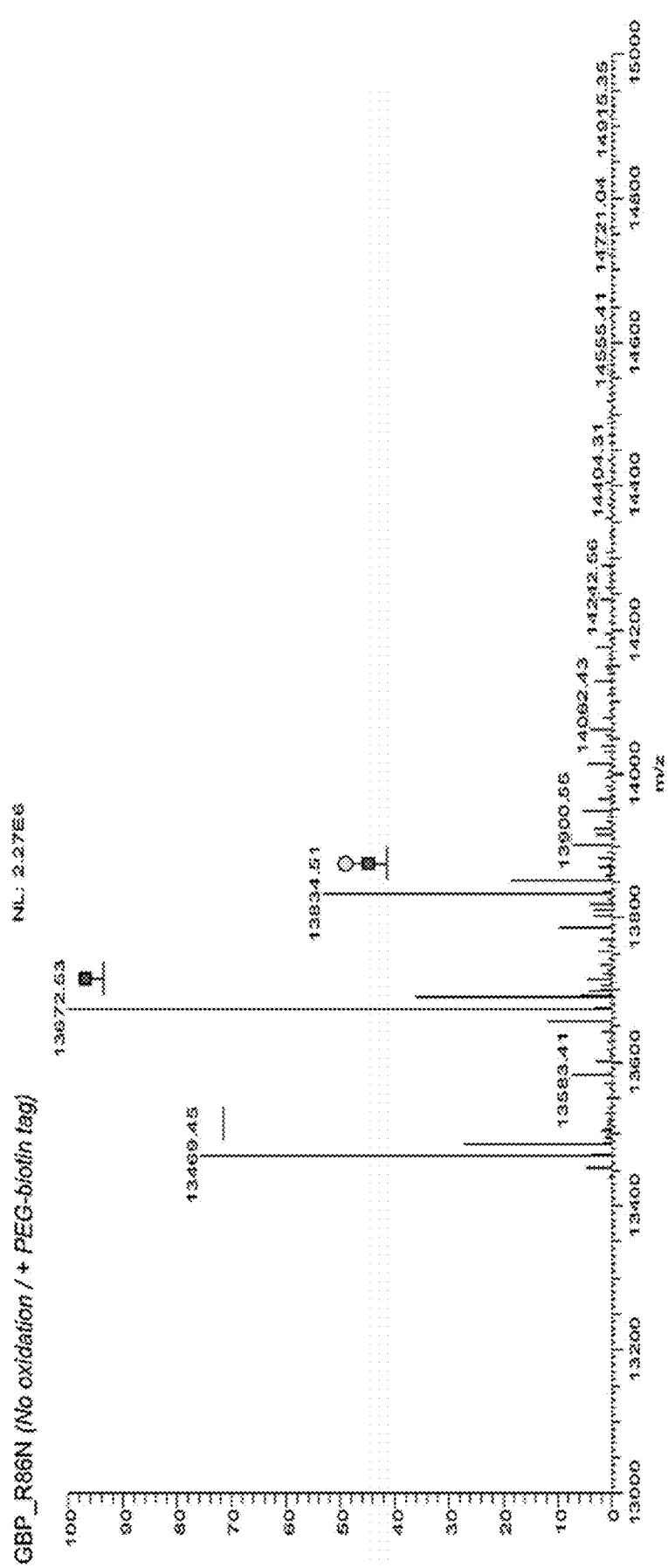

FIGS. 6A and 6B: GBP_R86N was recombinantly produced in *Pichia* GlycoDelete cells which co-express a galactosyltransferase. (FIG. 6A) Proteins were purified, yielding a mixture of non-glycosylated protein and protein carrying a GlcNAc or LacNAc N-glycan. (FIG. 6B) The purified protein was then oxidized with GAO or mock treated, and linked to a short biotinylated and aminooxy-modified PEG tag in a one-pot reaction. Mass spec analysis showed that the PEG tag was selectively linked to LacNAc-carrying GBP that was oxidized using GAO.

Figure 7A:
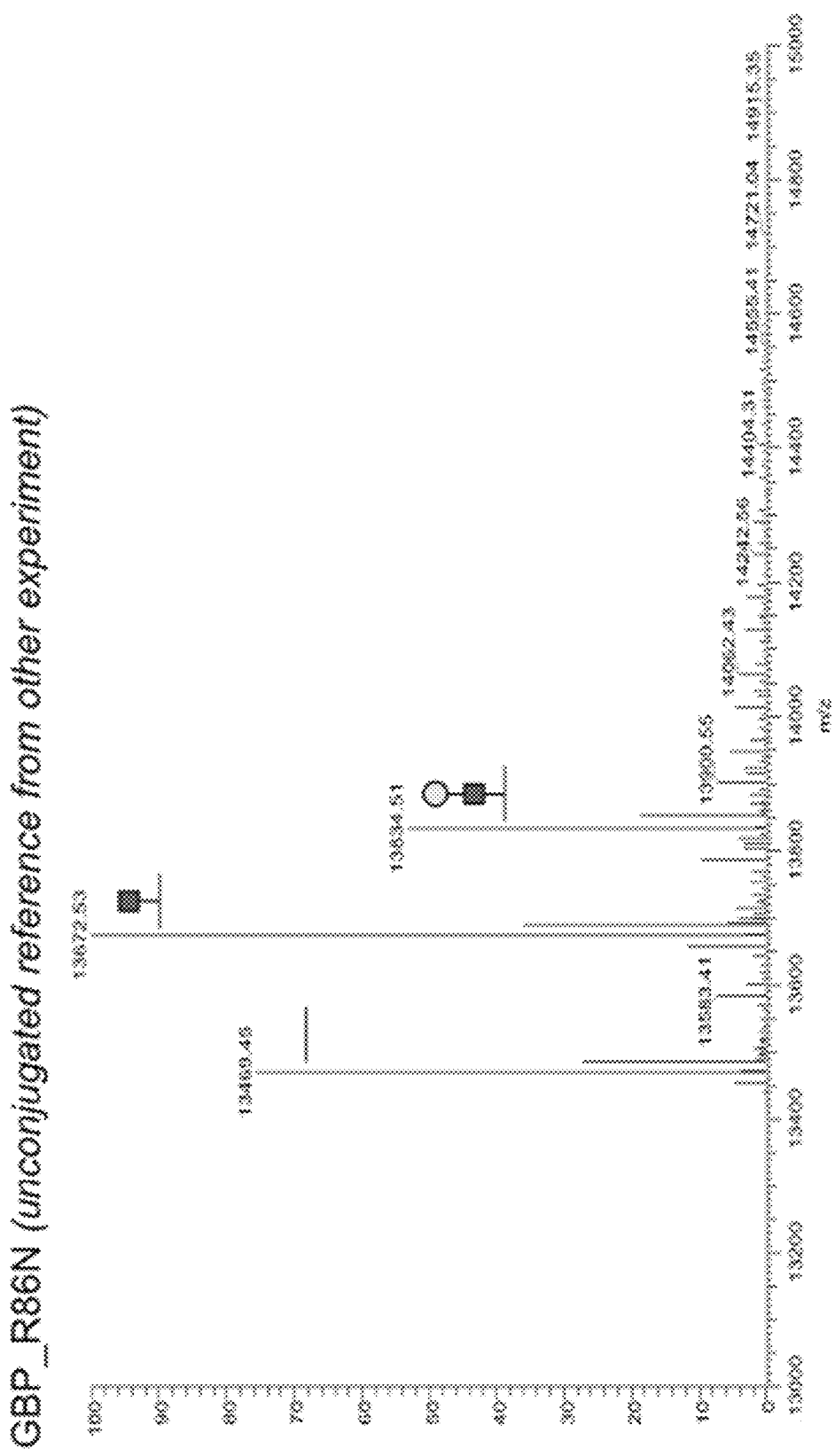
Figure 7B:
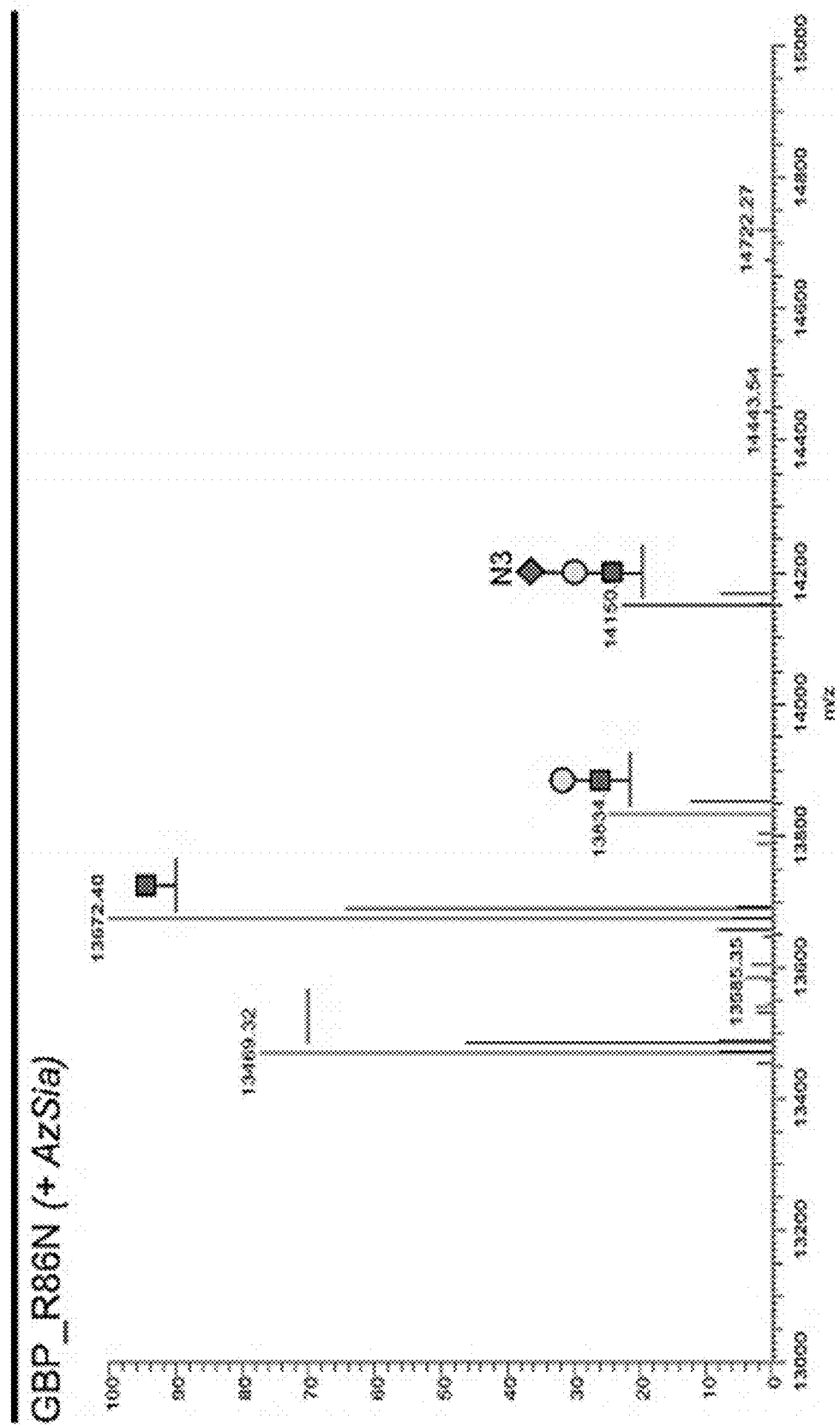
Figure 7C:
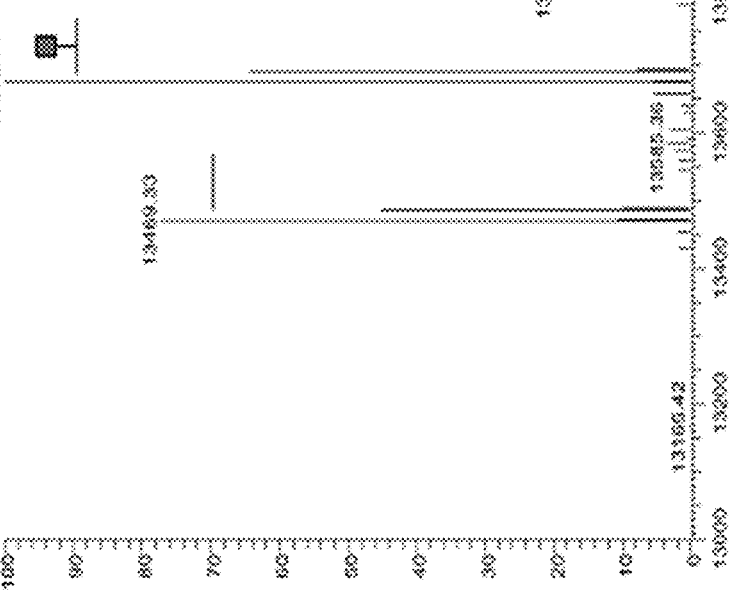
Figure 7C:

FIGS. 7A and 7B: GBP_R86N was recombinantly produced in *Pichia* GlycoDelete cells which co-express a galactosyltransferase. (FIG. 7A) Proteins were purified, yielding a mixture of non-glycosylated protein and protein carrying a GlcNAc or LacNAc N-glycan. (FIG. 7B) The purified protein was then incubated with CMP-Azido-Sialic Acid and recombinant hST6Gal1 enzyme to add an AzSia residue to the LacNAc chain, and subsequently subjected to a click reaction with a short biotinylated and DBCO-modified PEG tag. (FIG. 7C) Mass spec analysis showed that the PEG tag was selectively linked to LacNAc-carrying GBP that was modified with AzSia. The spectrum on top represents data from another experiment, and is included as a reference non-conjugated GBP_R86N.

DETAILED DESCRIPTION OF THE INVENTION

The present invention will be described with respect to particular embodiments and with reference to certain drawings, but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 4th ed., Cold Spring Harbor Press, Plainsview, N.Y. (2012); and Ausubel et al., Current Protocols in Molecular Biology (Supplement 114), John Wiley & Sons, New York (2016), for definitions and terms of the art. The definitions provided herein should not be construed to have a scope less than understood by a person of ordinary skill in the art.

As used herein, the term "nucleotide sequence" refers to a polymeric form of nucleotides of any length, either deoxyribonucleotides or ribonucleotides, or analogs thereof. Nucleotide sequences may have any three-dimensional structure, and may perform any function, known or unknown. Non-limiting examples of nucleotide sequences include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleotide sequence may be linear or circular.

As used herein, the term "polypeptide" refers to a polymeric form of amino acids of any length, which can include coded and non-coded amino acids, chemically or biochemically modified or derivatized amino acids, and polypeptides having modified peptide backbones. Polypeptide sequences can be depicted with the single-letter (or one letter) amino acid code or the three letter amino acid code as depicted here below:

| Amino acid | Three letter code | One letter code |
|---|---|---|
| alanine | ala | A |
| arginine | arg | R |
| asparagine | asn | N |

-continued

| Amino acid | Three letter code | One letter code |
|---|---|---|
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The term "Glycosylation acceptor site" refers to a position within a polypeptide which can be N- or O-glycosylated. N-linked glycans are typically attached to Asparagine (Asn), while O-linked glycans are commonly linked to the hydroxyl oxygen of serine, threonine, tyrosine, hydroxylysine, or hydroxyproline side-chains.

The term "N-glycosylation acceptor site" refers to a position within a polypeptide which can be N-glycosylated. N-linked glycans are typically attached to Asparagine (Asn) which resides in a consensus site. An "NXT", "NXS", "NXC" or "NXV" motif refers to the consensus sequences Asn-Xaa-Thr/Ser or Asn-Xaa-Cys/Val, wherein Xaa can be any amino acid except proline (Shrimal, S. and Gilmore, R., *J Cell Sci.* 126(23), 2013, Sun, S. and Zhang, H., *Anal. Chem.* 87 (24), 2015). It is well known in the art that potential N-glycosylation acceptor sites are specific to the consensus sequence Asn-Xaa-Thr/Ser or Asn-Xaa-Cys/Val. It has been shown in the art that the presence of proline between Asn and Thr/Ser leads to inefficient N-glycosylation.

The term "expression vector", as used herein, includes any vector known to the skilled person, including plasmid vectors, cosmid vectors, phage vectors, such as lambda phage, viral vectors, such as adenoviral, AAV or baculoviral vectors, or artificial chromosome vectors such as bacterial artificial chromosomes (BAC), yeast artificial chromosomes (YAC), or P1 artificial chromosomes (PAC). Expression vectors generally contain a desired coding sequence and appropriate promoter sequences necessary for the expression of the operably linked coding sequence in a particular host organism (e.g. higher eukaryotes, lower eukaryotes). Typically, a vector comprises a nucleotide sequence in which an expressible promoter or regulatory nucleotide sequence is operatively linked to, or associated with, a nucleotide sequence or DNA region that codes for an mRNA, such that the regulatory nucleotide sequence is able to regulate transcription or expression of the associated nucleotide sequence. Typically, a regulatory nucleotide sequence or promoter of the vector is not operatively linked to the associated nucleotide sequence as found in nature, hence is heterologous to the coding sequence of the DNA region operably linked to. The term "operatively" or "operably" "linked" as used herein refers to a functional linkage between the expressible promoter sequence and the DNA region or gene of interest, such that the promoter sequence is able to initiate transcription of the gene of interest, and refers to a functional linkage between the gene of interest and the transcription terminating sequence to assure adequate termination of transcription in eukaryotic cells. In addition, the term refers to the linkage (or fusion) between a targeting sequence and the open reading frame of an enzyme. An "inducible promoter" refers to a promoter that can be switched 'on' or 'off' (thereby regulating gene transcription) in response to external stimuli such as, but not limited to, temperature, pH, certain nutrients, specific cellular signals, et cetera. It is used to distinguish between a "constitutive promoter", by which a promoter is meant that is continuously switched 'on', i.e. from which gene transcription is constitutively active.

A "glycan" generally refers in the art to glycosidically linked monosaccharides, oligosaccharides and polysaccharides. Hence, carbohydrate portions of a glycoconjugate, such as a glycoprotein, glycolipid, or a proteoglycan are referred to herein as a "glycan". Glycans can be homo- or heteropolymers of monosaccharide residues, and can be linear or branched. Generally N-linked glycans may be composed of GalNAc, Galactose, neuraminic acid, N-acetylglucosamine, Fucose, Mannose, and other monosaccharides, as also exemplified further herein.

In eukaryotes, O-linked glycans are assembled one sugar at a time on a serine or threonine residue of a peptide chain in the Golgi apparatus. Unlike N-linked glycans, there are no known consensus sequences but the position of a proline residue at either −1 or +3 relative to the serine or threonine is favourable for O-linked glycosylation.

"Complex N-glycans" in the art refers to structures with typically one, two or more (e.g. up to six) outer branches, most often linked to an inner core structure Man3GlcNAc2. The term "complex N-glycans" is well known to the skilled person and defined in literature. For instance, a complex N-glycan may have at least one branch, or at least two, of alternating GlcNAc and optionally also Galactose (Gal) residues that may terminate in a variety of oligosaccharides but typically will not terminate with a Mannose residue. For the sake of clarity a single GlcNAc, LacNAc (=GlcNAc-Gal), sialyl-LacNAc present on an N-glycosylation site of a glycoprotein (thus lacking the inner core structure Man3GlcNAc2) is not regarded as a complex N-glycan.

'Glycoproteins' as used in the application refers to proteins that, in their normal physiological context and/or their functional form, contain oligosaccharide chains (N-glycans) covalently attached to their polypeptide side-chains. In addition, a glycoprotein comprises also proteins with an artificially introduced glycosylation site, particularly an artificially introduced N-glycosylation site. Typically, a glycoprotein, typically a recombinant glycoprotein, for example a heterologous recombinant glycoprotein (which does not occur normally in the eukaryotic organism) is produced as several glycoforms when it is made in a eukaryotic organism such as a N-glycosylation-engineered eukaryotic organism. To further illustrate this, when a N-linked glycoprotein, comprising one N-glycan acceptor glycosylation site is produced, according to claim 1 of the present invention in a eukaryotic host such as a mammalian host, then the following situations can occur: i) the N-glycan acceptor site carries no N-glycan—in this case an unglycosylated glycoprotein is produced, ii) N-glycans consisting of a GlcNAc residue can be formed, iii) N-glycans consisting of a LacNAc residue can be formed and iv) a fraction of aberrant N-glycans are present of which structure is unpredictable and depends on the host and on the nature of the glycoprotein. Such aberrant N-glycans can for example comprise N-glycosylation structures which are not completely processed by the exogenous endoglucosaminidase and for example fucose-linked GlcNAc structures as described in Felix J. et al (2015) Structure 23, 1621-1631. Thus, a glycoform is an N-glycosylated form a glycoprotein meaning that an unglycosylated glycoprotein is not a glycoform. Thus, a glycoprotein comprising one N-glycan glycosylation site produced according to claim 1, predominantly consists of more than 80%, 90%, or even more than 95% of 2 different glycoforms (id est a N-glycosylated glycoprotein comprising N-glycans consisting of a GlcNAc residue and a N-glycosylated glycoprotein comprising N-glycans consisting of a LacNAc disaccharide. Thus, different glycoforms (even originating from one specific functional N-glycosylation site on a (recombinant) glycoprotein) occur because of the very nature of the (engineering) process of N-glycosylation of which each step is not 100% efficient. A non-limiting list of glycoproteins is provided in the specification. The term 'glycoproteins' is not intended to refer to the length of the amino acid chain, 'glycopeptides' are included within the definition of 'glycoproteins'.

The terms '(glyco)protein' and 'enzyme' (e.g. endoglucosaminidase, glycosyltransferase, mannosidase, mannosyltransferase) as used in the application are also intended to cover functionally active fragments and variants of the naturally occurring proteins. Indeed, for many (e.g. therapeutic) proteins, part of the protein may be sufficient to achieve an (e.g. therapeutic, enzymatic) effect. The same applies for variants (i.e. proteins in which one or more amino acids have been substituted with other amino acids, but which retain functionality or even show improved functionality), in particular for variants of the enzymes optimized for enzymatic activity. In the context of the application, a glycoprotein refers to the protein itself; a glycoprotein may be either in its glycosylated or non-glycosylated form. A 'glycosylated' protein is a (glyco)protein that carries at least one oligosaccharide chain. An N-glycosylated protein, particularly an N-glycosylated recombinant glycoprotein, is a glycoprotein which carries at least one oligosaccharide chain on an N-glycan.

The nature of the glycoprotein is not critical to the invention, but glycoproteins will typically be proteins relevant for medicine and/or industry for which homogeneous N-glycosylation is important. Non-limiting examples include many hormones, growth factors, cytokines and their corresponding receptors, such as follicle-stimulating hormone (FSH), luteinizing hormone (LH), thyroid-stimulating hormone (TSH), epidermal growth factor (EGF), human epidermal growth factor receptor-2 (HER-2), fibroblast growth factor-alpha (FGF-α), fibroblast growth factor-beta (FGF-β), transforming growth factor-alpha (TGF-α), transforming growth factor-beta (TGF-β), platelet-derived growth factor (PDGF), insulin-like growth factor-1 (IGF-1), insulin-like growth factor-2 (IGF-2), nerve growth factor (NGF), nerve growth factor-beta (NGF-β); receptors of the aforementioned, growth hormones (e.g., human growth hormone, bovine growth hormone); insulin (e.g., insulin A chain and insulin B chain), proinsulin; erythropoietin (EPO); colony stimulating factors (e.g., granulocyte colony-stimulating factor (G-CSF), granulocyte macrophage colony-stimulating factor (GM-CSF), macrophage colony-stimulating factor (M-CSF)); interleukins (e.g., IL-1 through IL-33); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; calcitonin; CD proteins (e.g., CD3, CD4, CD8, CD28, CD19, etc.); CTLA proteins (e.g., CTLA4); T-cell and B-cell receptor proteins; antibodies, bone morphogenic proteins (BMPs, e.g., BMP-1, BMP-2, BMP-3, etc.); neurotrophic factors, e.g., bone derived neurotrophic factor (BDNF); neurotrophins, e.g., NT3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; alkaline phosphatase; lectins; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art, including fusion or chimeric proteins of the above.

A 'glycoform' as used in the present invention is a variant of a glycosylated glycoprotein wherein the variation is in the N-glycan composition present on said glycoprotein. Typically, glycoforms in the present invention comprise N-glycan structures consisting of GlcNAc and LacNAc (which is GlcNAc-Gal).

An 'endoglucosaminidase' as used herein refers to enzymes that hydrolyse the bond between the anomeric carbon of a non-terminal beta-linked N-acetylglucosamine residue in an oligosaccharide of a glycoprotein or a glycolipid, and its aglycon, thereby releasing mono- or oligosaccharides from glycoproteins or glycolipids or sugar polymers. Endoglucosaminidases are a subset of the glycosidases, and may or may not have other enzymatic activities (such as e.g. glycosyltransferase activity). A particular class of endoglucosaminidases is formed by the endo-β-N-acetylglucosaminidases or mannosyl-glycoprotein endo-β-N-acetylglucosaminidases, indicated as EC 3.2.1.96 in the International Union of Biochemistry and Molecular Biology (IUBMB) nomenclature. This particular class of enzymes are capable of catalyzing the endohydrolysis of the N,N'-diacetylchitobiosyl unit in high-mannose glycopeptides and glycoproteins containing the -[Man (GlcNAc)$_2$]Asn- structure. One N-acetyl-D-glucosamine (GlcNAc) residue remains attached to the protein; the rest of the oligosaccharide is released intact. The result thus is a single GlcNAc-modified N-glycosylation site present on a glycoprotein. A particular preferred class of endoglucosaminidases is formed by the mannosyl-glycoprotein endo-β-N-acetylglucosaminidases, indicated as EC 3.2.1.96 in the IUBMB nomenclature. These enzymes can remove sugar chains (hybrid N-glycans, high mannose N-glycans and neoglycoforms of N-glycans as shown herein) while leaving one GlcNAc residue on the protein. Examples of these include, but are not limited to Endo A, Endo BH, Endo CE, Endo D, Endo F1, Endo H, Endo M, Endo T (see also WO2006/050584), and ENGase. Other examples are known to the skilled person and can for instance be found on www.cazy.org, in particular under the Glycoside Hydrolase Family 85 and 18. Particularly envisaged is the use of the Endo T enzyme from *Hypocrea jecorina* (formerly known as *Trichoderma reesei*) that is described in WO2006/050584 (see e.g. SEQ IDs 9-12 therein).

A 'glycosyltransferase' as used in the application is any of a group of enzymes that catalyze the transfer of glycosyl groups in biochemical reactions, in particular glycosyl transfer to asparagine-linked sugar residues to give N-linked glycoproteins. Glycosyltransferases fall under EC 2.4 in the IUBMB nomenclature, a particular class of glycosyltransferases are hexosyltransferases (EC 2.4.1). Among the wide variety of these post-translational enzymes that process peptides into glycoproteins are enzymes such as, but not limited to, N-acetylglucosaminyl transferases, N-acetylgalactosaminyltransferases, sialyltransferases, fucosyltransferases, galactosyltransferases, and mannosyltransferases.

Note that exogenous mannosyltransferases are excluded for specific embodiments of N-glycosylation-engineered yeast cells described in the application. 'Mannosyltransferases' as used in the application refers to enzymes that catalyze the transfer of a mannosyl group to an acceptor molecule, typically another carbohydrate, in the Golgi apparatus. Mannosyltransferases are typically endogenous enzymes in fungi and yeast and involved in the synthesis of high-mannose type glycans.

A "higher eukaryotic cell" as used herein refers to eukaryotic cells that are not cells from unicellular organisms. In other words, a higher eukaryotic cell is a cell from (or derived from, in case of cell cultures) a multicellular eukaryote such as a human cell line or another mammalian cell line (e.g. a CHO cell line). Particularly, the term generally refers to mammalian cells, human cell lines and insect cell lines. More particularly, the term refers to vertebrate cells, even more particularly to mammalian cells or human cells. The higher eukaryotic cells as described herein will typically be part of a cell culture (e.g. a cell line, such as a HEK or CHO cell line).

By "lower eukaryotic cell" a filamentous fungus cell or a yeast cell is meant. Yeast cells can be from the species *Saccharomyces* (e.g. *Saccharomyces cerevisiae*), *Hansenula* (e.g. *Hansenula polymorpha*), *Arxula* (e.g. *Arxula adeninivorans*), *Yarrowia* (e.g. *Yarrowia lipolytica*), *Kluyveromyces* (e.g. *Kluyveromyces lactis*), or *Komagataella phaffii* (Kurtzman, C. P. (2009) *J Ind Microbiol Biotechnol*. 36(11) which was previously named and better known under the old nomenclature as *Pichia pastoris* and further used herein. According to a specific embodiment, the lower eukaryotic cells are *Pichia* cells, and in a most particular embodiment *Pichia pastoris* cells. In specific embodiments the filamentous fungus cell is *Myceliopthora thermophila* (also known as C1 by the company Dyadic), *Aspergillus* species (e.g. *Aspergillus nidulans, Aspergillus niger, Aspergillus oryzae, Aspergillus japonicus*), *Fusarium* species (e.g. *Fusarium venenatum*), *Hypocrea* and *Trichoderma* species (e.g. *Trichoderma reesei*).

Essential to the present invention, the "lower or higher eukaryotic cell" of the present invention is a glyco-engineered cell. A "glyco-engineered cell" refers to a cell that has been genetically modified so that it expresses proteins with an altered N-glycan structure and/or O-glycan structure as compared to in a wild type background. Typically, the naturally occurring modifications on glycoproteins have been altered by genetic engineering of enzymes involved in the glycosylation pathway. In general, sugar chains in N-linked glycosylation may be divided in three types: high-mannose (typically yeast), complex (typically mammalian) and hybrid type glycosylation. Besides that, a variety of O-glycan patterns exist, for example with yeast oligomannosylglycans differing from mucin-type O-glycosylation in mammalian cells. The different types of N- and O-glycosylation are all well known to the skilled person and defined in the literature. Considerable effort has been directed towards the identification and optimization of strategies for the engineering of eukaryotic cells that produce glycoproteins having a desired N-and/or O-glycosylation pattern and are known in the art (e.g. De Pourcq, K. et al., Appl Microbiol Biotechnol. 87(5), 2010).

In the present invention the glyco-engineered cells (or the glyco-engineered expression system) which are used are described in patent applications WO2010015722 and WO2015032899 (further designated herein as GlycoDelete cells, or cells having a GlycoDelete background) and in Meuris L. et al (2014) *Nat. Biotechn.* 32(5) 485) and relates to a eukaryotic cell expressing both at least an endoglucosaminidase enzyme and a target protein, and wherein the recombinant secreted target proteins are characterized by a uniform N-glycosylation pattern (in particular one single GlcNAc residue (in lower eukaryotes) or a modification thereof such as GlcNAc modified with Galactose (LacNAc) or sialyl-LacNAc (in mammalian cells). Particularly preferred in the present invention are higher eukaryotic cells which have a GlycoDelete background. Lower eukaryotic cells having a GlycoDelete background produce N-glycans having one single GlcNAc residue.

An 'ER localization signal' or a 'Golgi localization signal' is a molecule, typically a peptide that directs localization of the polypeptide or protein to which it is conjugated to the ER or Golgi apparatus, respectively. Localization thus also implies retention in the ER or Golgi apparatus, respectively. Typically, these localization (or retention) sequences are peptide sequences derived from (pre)proteins that are situated in the ER or Golgi when functionally active as a mature protein.

The term 'beta-1,4-galactosyltransferase' in the present invention refers to an enzyme that has exclusive specificity for the donor substrate UDP-galactose; all transfer galactose in a beta1,4 linkage to similar acceptor sugars: GlcNAc, Glc, and Xyl. In the present invention the beta-1,4-galactosyltransferase adds galactose to N-acetylglucosamine residues that are either monosaccharides or the nonreducing ends of glycoprotein carbohydrate chains. Particularly preferred beta-1,4-galactosyltransferases are of the mammalian type, even more particularly are of the human type.

The term 'UDP-N-acetylglucosamine-2-epimerase/N-acetylmannosamine kinase' in the present invention refers to a a bifunctional enzyme that initiates and regulates the biosynthesis of N-acetylneuraminic acid (NeuAc), a precursor of sialic acids. It is a rate-limiting enzyme in the sialic acid biosynthetic pathway. The enzyme is allosterically regulated and hence is subject to feedback inhibition by cytidine monophosphate-N-acetylneuraminic acid (CMP-Neu5Ac), the end product of neuraminic acid biosynthesis.

Hence a eukaryotic cell lacking 'UDP-N-acetylglucosamine-2-epimerase/N-acetylmannosamine kinase' in the present invention can refer to a lower eukaryotic cell which—by nature—does not possess this enzyme. Alternatively, it refers to a higher eukaryotic cell which has a gene disruption (or a gene deletion or a mutation which generates a non-functional enzyme) in this enzyme.

The term 'UDP-Glc-4-epimerase' refers to the enzyme UDP-glucose 4-epimerase also known as UDP-galactose 4-epimerase or GalE, which is a homodimeric epimerase found in bacterial, fungal, plant, and mammalian cells. This enzyme performs the final step in the Leloir pathway of galactose metabolism, catalyzing the reversible conversion of UDP-galactose to UDP-glucose.

The term 'UDP-galactose transporter' refers to the enzyme which transports nucleotide sugars (such as UDP-galactose) from the cytosol into the Golgi vesicles where glycosyltransferases (such as the galactosyltransferase) function. Alternative names for the enzyme 'UDP-galactose transporter' are "UDP-galactose transmembrane transporter' or 'UDP-galactose translocator' or 'Solute carrier family 35 member A2'. The introduction of an exogenous 'UDP-galactose transporter' as an exogenous nucleic acid sequence in a eukaryotic host cell is particularly relevant for hosts which do not make endogenous UDP-Galactose.

Accordingly, the present invention provides in a first embodiment a eukaryotic cell comprising:
- a first exogenous nucleic acid sequence encoding an endoglucosaminidase enzyme,
- a second exogenous nucleic acid sequence encoding a glycoprotein.

wherein said eukaryotic cell produces no detectable N-glycans, comprising sialic acid residues, present on glycoproteins.

In yet another embodiment the invention provides a eukaryotic cell comprising:
- a first exogenous nucleic acid sequence encoding an endoglucosaminidase enzyme,
- a second exogenous nucleic acid sequence encoding a glycoprotein.

wherein said eukaryotic cell produces less than 5% N-glycans comprising sialic acid residues, present on glycoproteins.

Eukaryotic cells which produce no detectable N-glycans comprising sialic acid residues on glycoproteins or eukaryotic cells which produces less than 5% N-glycans comprising sialic acid residues on glycoproteins do not have (id est by nature or by engineering (e.g. mutation) the biosynthetic capability to produce the sugar nucleotide precursor cytidine monophosphate (CMP)-sialic acid [specifically, CMP-N-acetylneuraminic acid (CMP-NANA)], do not have the transporter to shuttle CMP-sialic acid into the Golgi (id est by nature or by mutation) and/or do not have a sialic acid transferase enzyme to transfer sialic acid to terminal galactoses (id est by nature or by mutation). Examples of enzymes involved in the biosynthesis of CMP-NANA comprise UDP-N-acetylglucosamine-2-epimerase/N-acetylmannosamine kinase (GNE), N-acetylneuraminate-9-phosphate synthase and CMP-sialic acid synthase. The transporter to shuttle CMP-NANA into the Golgi is the CMP-sialic acid transporter. Sialyltransferases are classified based on the position of the glycosyl acceptor that N-acetylneuraminic acid (NANA or Neu5Ac) is transferred to. In humans, these are ST3, ST6, and ST8, which form an α-glycosidic bond between the C2 atom of Neu5Ac and the 3'-, 6'-, or 8'-hydroxyl group of the acceptor, respectively.

The invention provides in a further embodiment a eukaryotic cell lacking UDP-N-acetylglucosamine-2-epimerase/N-acetylmannosamine kinase activity comprising:
- a first exogenous nucleic acid sequence encoding an endoglucosaminidase enzyme,
- optionally a second exogenous nucleic acid sequence encoding a beta-(1,4)-galactosyltransferase, and
- a third exogenous nucleic acid sequence encoding a glycoprotein.

In yet another embodiment the invention provides a eukaryotic cell producing no detectable levels of N-glycans comprising sialic acid on glycoproteins said eukaryotic cell comprises
- a first exogenous nucleic acid sequence encoding an endoglucosaminidase enzyme,
- a second exogenous nucleic acid sequence encoding a glycoprotein, and
- optionally a third exogenous nucleic acid sequence encoding a beta-1-4-galactosyltransferase.

In yet another embodiment the invention provides a eukaryotic cell lacking UDP-N-acetylglucosamine-2-epimerase/N-acetylmannosamine kinase enzymatic activity and lacking UDP-Glc-4-epimerase activity comprising:

a first exogenous nucleic acid sequence encoding an endoglucosaminidase enzyme, a second exogenous nucleic acid sequence encoding a glycoprotein, and optionally a third exogenous nucleic acid sequence encoding a beta-1-4-galactosyltransferase.

Higher eukaryotic cells lacking UDP-Glc-4-epimerase activity (GalE) and having an exogenous endoglucosaminidase enzyme which is expressed in said cells are described in the application WO2017005925 (such high eukaryotic cells are herein also referred to as GlucoDoubleDelete cells or higher eukaryotic cells having a GlycoDoubleDelete background). The latter cells do not produce glycans comprising galactose-residues and these cells also lack O-glycosylation (id est the O-glycans do not have galactose and GalNAc residues) on their glycoproteins because of the deficiency in GalE. Interestingly, feeding of galactose to such higher eukaryotic cells lacking GalE activity and expressing an exogenous endoglucosaminidase enzyme and an exogenous glycoprotein, leads to galactosylated N-glycans only and not to galactosylated O-glycans. Thus eukaryotic cells lacking UDP-Glc-4-epimerase activity (GalE) and lacking UDP-N-acetylglucosamine-2-epimerase/N-acetylmannosamine kinase enzymatic activity and having an exogenous endoglucosaminidase enzyme expressed in said cells produce glycoproteins which N-glycans consisting of LacNAc structures.

In yet another embodiment the invention provides a eukaryotic cell producing no detectable levels of N-glycans comprising sialic acid on glycoproteins said eukaryotic cell comprises a first exogenous nucleic acid sequence encoding an endoglucosaminidase enzyme, a second exogenous nucleic acid sequence encoding a glycoprotein, and optionally a third exogenous nucleic acid sequence encoding a beta-1-4-galactosyltransferase.

In yet another embodiment the invention provides a eukaryotic cell which is deficient in complex glycosylation and is deficient in UDP-N-acetylglucosamine-2-epimerase/N-acetylmannosamine kinase activity comprising:

a first exogenous nucleic acid sequence encoding an endoglucosaminidase enzyme, optionally a second exogenous nucleic acid sequence encoding a beta-(1,4)-galactosyltransferase, and a third exogenous nucleic acid sequence encoding a glycoprotein.

In yet another embodiment the invention provides a eukaryotic cell producing no detectable levels of N-glycans comprising sialic acid on glycoproteins said eukaryotic cell comprises a first exogenous nucleic acid sequence encoding an endoglucosaminidase enzyme, a second exogenous nucleic acid sequence encoding a glycoprotein, and optionally a third exogenous nucleic acid sequence encoding a beta-1-4-galactosyltransferase, optionally a third exogenous nucleic acid encoding an UDP-galactose transporter.

In yet another embodiment the invention provides a eukaryotic cell which is deficient in complex glycosylation and is deficient in UDP-N-acetylglucosamine-2-epimerase/N-acetylmannosamine kinase activity comprising:

a first exogenous nucleic acid sequence encoding an endoglucosaminidase enzyme, optionally a second exogenous nucleic acid sequence encoding a beta-(1,4)-galactosyltransferase, optionally a third exogenous nucleic acid sequence encoding an UDP-galactose transporter, and a fourth exogenous nucleic acid sequence encoding a glycoprotein.

In yet another embodiment the invention provides a lower eukaryotic cell which is deficient in complex glycosylation and is deficient in UDP-N-acetylglucosamine-2-epimerase/N-acetylmannosamine kinase activity comprising:

a first exogenous nucleic acid sequence encoding an endoglucosaminidase enzyme, a second exogenous nucleic acid sequence encoding a beta-(1,4)-galactosyltransferase, and a third exogenous nucleic acid sequence encoding a glycoprotein.

In a specific embodiment the higher eukaryotic cell which is deficient in complex glycosylation lacks enzymatic activity of an enzyme needed for complex glycosylation, selected from the group consisting of ER-mannosidase I, glucosidase I, glucosidase II, N-acetylglucosaminyl transferase I, N-acetylglucosaminyl transferase II or mannosidase II.

In a particular embodiment the higher eukaryotic cell which is deficient in complex glycosylation lacks enzymatic activity of N-acetylglucosaminyltransferase I.

Higher eukaryotic cells lacking (or 'being deficient in' or 'having a non-functional' are equivalent terms) UDP-N-acetylglucosamine-2-epimerase/N-acetylmannosamine kinase or are deficient in an enzyme needed for complex glycosylation may be engineered by a variety of gene editing approaches. For example, zinc finger nucleases (ZFN) are artificial restriction enzymes generated by fusing a zinc finger DNA-binding domain to a DNA-cleavage domain. Zinc finger domains can be engineered to target desired DNA sequences, which enables zinc-finger nucleases to target a unique sequence within a complex genome. By taking advantage of endogenous DNA repair machinery, these reagents can be used to precisely alter the genomes of simple and higher organisms. Other technologies for genome engineering that can be used to modify genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another recent and very popular genome editing technology is the CRISPR-Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway and has been modified to edit basically any genome. By delivering the Cas nuclease (in many cases Cas9) complexed with a synthetic guide RNA (gRNA) in a cell, the cell's genome can be cut at a desired location depending on the sequence of the gRNA, allowing existing genes to be removed and/or new one added and/or more subtly removing, replacing or inserting single nucleotides (e.g. DiCarlo et al 2013 Nucl Acids Res doi:10.1093/nar/gkt135; Sander & Joung 2014 Nat Biotech 32:347-355).

In a particular embodiment the exogenously introduced genes can be present on one single construct (e.g. a vector) or can be introduced as separate constructs.

In yet another particular embodiment the eukaryotic cells of the invention can further comprise other exogenous nucleic acid sequences such as an UDP-Glc-4-epimerase.

In preferred embodiments the eukaryotic cells of the invention, the endoglucosaminidase enzyme and/or the beta-1,4-galactosyltransferase enzymes are operably linked to an ER or Golgi localization signal.

In another embodiment the eukaryotic cells of the invention, the endoglucosaminase enzyme is operably linked to a secretion signal.

In another embodiment the invention the invention provides a composition comprising a plurality of N-glycosylated forms of a recombinant glycoprotein, wherein glycosylated forms comprising N-glycans consisting of GlcNAc residues and glycosylated forms comprising N-glycans consisting of LacNAc residues are present in said composition and wherein the amount of glycosylated forms comprising N-glycans consisting of LacNAc residues with respect to the glycosylated forms comprising N-glycans consisting of GlcNAc residues is at least 80%, or at least 85% or at least 90%.

In another specific embodiment the invention provides a composition comprising a plurality of glycoforms of a recombinant glycoprotein, wherein the N-glycans present on said glycoforms consist of a mixture of GlcNAc and LacNAc and wherein said N-glycans consisting of LacNAc are present at a level of higher than 80%, or higher than 85% or even higher than 90% of the total N-glycans in said composition.

In another specific embodiment the invention provides a composition comprising a plurality of glycoforms of a recombinant glycoprotein, wherein the N-glycans present on said glycoforms comprise a mixture of GlcNAc residues and LacNAc disaccharides and wherein said N-glycans consisting of LacNAc disaccharides are present at a level of higher than 80%, or higher than 85% or even higher than 90% of the pool of N-glycans consisting of LacNAc disaccharides and N-glycans consisting of GlcNAc residues in said composition.

In another specific embodiment the invention provides a composition comprising a plurality of glycoforms of a recombinant monoclonal antibody, wherein the N-glycans present on the Fc region of said glycoforms comprise a mixture of GlcNAc and LacNAc and wherein said N-glycans consisting of LacNAc are present at a level of higher than 80%, or at a level of higher than 85% or at a level of higher than 90% of the total N-glycans in said composition.

In yet another embodiment the invention provides a composition according to the invention wherein the glycoprotein present in said composition is selected from the list comprising a growth factor, an antibody, a single domain antibody, an antibody fragment, a vaccine, a regulatory protein, a cytokine, a membrane protein, an antigen, a receptor, a VHH.

In yet another embodiment the invention provides specific compositions of GM-CSF, particularly hGM-CSF.

Granulocyte-macrophage colony-stimulating factor (GM-CSF) is a cytokine that enhances activation of dendritic cells for antigen presentation and potentiates T- and B-lymphocyte antitumor functions. Systemic administration of GM-CSF has activity in prostate and ovarian carcinoma and is being evaluated in phase 3 adjuvant trials for melanoma and lymphoma. Sargramostim (tradename Leukine) is a recombinant granulocyte macrophage colony-stimulating factor (GM-CSF) that functions as an immunostimulator. Sargramostim is a recombinant version of GM-CSF, which is a glycoprotein made of 127 amino acids; sargramostim is mixture of three versions of GM-CSF that have molecular weights of 19,500, 16,800 and 15,500 Daltons. It is manufactured in yeast. Sargramostim is primarily used for myeloid reconstitution after autologous or allogeneic bone marrow transplantation. It is also used to treat neutropenia induced by chemotherapy during the treatment of acute myeloid leukemia. It also used as a medical countermeasure for treating people who have been exposed to sufficient radiation to suppress bone marrow myelogenesis. Also GM-CSF has utility to prevent mortality from heavy infections in people who have been exposed to excessive radiation. The product is administered via intravenous infusion. Some people have experienced anaphylaxis when given this drug, and infusion reactions have occurred as well, including edema, capillary leak syndrome, a buildup of fluid around the lungs and around the heart. Irregular heart rhythms have occurred, especially in people with a history of that problem. The product suppresses some white blood cells, and may even promote tumor growth. It would be desirable to obtain GM-CSF formulations which have more favorable pharmacokinetics, in order to obtain GM-CSF variants and formulations with a longer half-life in circulation. Therefore there is a need for alternative compositions of GM-CSF, Therefore, in yet another embodiment the invention provides a composition comprising a plurality of N-glycosylated forms of GM-CSF, wherein no N-glycans comprising sialic acid residues and no mucin-type O-glycans are present on GM-CSF, wherein the N-glycosylated forms of GM-CSF comprise N-glycans consisting of a mixture of GlcNAc residues and LacNAc disaccharides, and wherein said N-glycans consisting of LacNAc disaccharides are present at a level of higher than 70%, at a level higher than 80%, at a level higher than 85% or at a level of higher than 90% of the pool of N-glycans consisting of LacNAc disaccharides and N-glycans consisting of GlcNAc in said composition.

In yet another embodiment the invention provides a composition comprising a conjugate comprising a glycosylated form of GM-CSF comprising N-glycans consisting of LacNAc disaccharides and a conjugated moiety, wherein said moiety is linked to a N-glycan consisting of LacNAc disaccharide present on GM-CSF, said glycosylated form of GM-CSF consisting of LacNAc disaccharides being present in a composition comprising a plurality of N-glycosylated forms of GM-CSF, wherein no N-glycans comprising sialic acid residues and no mucin-type O-glycans are present on GM-CSF, wherein N-glycosylated forms of GM-CSF comprise N-glycans consisting of a mixture of GlcNAc residues and LacNAc disaccharides, and wherein said N-glycans consisting of LacNAc disaccharide are present at a level of higher than 70%, at a level higher than 80%, at a level higher than 85% or at a level of higher than 90% of the pool of N-glycans consisting of LacNAc disaccharides and N-glycans consisting of GlcNAc residues in said composition.

In yet another embodiment the invention provides a method to produce a composition as herein defined before comprising: i) providing a eukaryotic cell which produces no detectable N-glycans comprising terminal sialic acid residues, said eukaryotic cell comprising a first exogenous nucleic acid encoding an endoglucosaminidase enzyme and a second exogenous nucleic acid sequence encoding a glycoprotein.

In yet another embodiment the invention provides a method to produce a composition as herein defined before comprising i) providing a eukaryotic cell which is deficient in complex glycosylation and is deficient in UDP-N-acetyl-glucosamine-2-epimerase/N-acetylmannosamine kinase activity comprising:
  a first exogenous nucleic acid sequence encoding an endoglucosaminidase enzyme,
  optionally a second exogenous nucleic acid sequence encoding a beta-(1,4)-galactosyltransferase,
  optionally a third exogenous nucleic acid sequence encoding an UDP-galactose transporter, and
  a fourth exogenous nucleic acid sequence encoding a glycoprotein.

In yet another embodiment the invention provides a composition of the invention for for use as a medicament.

In yet another embodiment the invention provides a pharmaceutical composition comprising a composition of the invention.

In yet another embodiment the invention provides a method to produce a composition of the invention said method comprising introducing an expression vector comprising a nucleotide sequence encoding a glycoprotein in a eukaryotic cell having a GlycoDelete background (or "a GlycoDelete engineered eukaryotic cell" which is an equivalent wording) which cell lacks expression of UDP-N-acetyl-glucosamine-2-epimerase/N-acetylmannosamine kinase, which eukaryotic cell comprises a first exogenous nucleic acid sequence encoding an endoglucosaminidase enzyme, optionally a second exogenous nucleic acid sequence encoding a beta-(1,4)-galactosyltransferase; expressing said glycoprotein and isolating the resulting glycoprotein form the cells of from the growth medium.

In yet another embodiment the invention provides a method to produce a composition of the invention said method comprising introducing an expression vector comprising a nucleotide sequence encoding a glycoprotein in a GlycoDelete-engineered eukaryotic cell which cell lacks expression of UDP-N-acetylglucosamine-2-epimerase/N-acetylmannosamine kinase and which eukaryotic cell lacks ER-mannosidase I activity or glucosidase I activity or glucosidase II activity or N-acetylglucosaminyl transferase I activity or N-acetylglucosaminyl transferase II activity or mannosidase II enzymatic activity, which eukaryotic cell comprises a first exogenous nucleic acid sequence encoding an endoglucosaminidase enzyme, optionally a second exogenous nucleic acid sequence encoding a beta-(1,4)-galactosyltransferase; expressing said glycoprotein and isolating the resulting glycoprotein form the cells of from the growth medium.

In particular higher eukaryotic cells which can be engineered towards a GlycoDelete background can be of any higher eukaryotic organism, but in particular embodiments mammalian cells are envisaged. The nature of the cells used will typically depend on the desired glycosylation properties and/or the ease and cost of producing the polypeptide described herein. Mammalian cells may for instance be used to avoid problems with immunogenicity. Higher eukaryotic cell lines for protein production are well known in the art, including cell lines with modified glycosylation pathways. Non-limiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, Som. Cell Molec. Genet., 12:555-556; and Kolkekar et al., 1997, Biochemistry, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/-DHFR, Urlaub and Chasin, 1980, Proc. Natl. Acad. Sci. USA, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, J. Gen. Virol., 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, Annals NYAcad. Sci., 383:44-68); MCR 5 cells; FS4 cells. According to particular embodiments, the cells are mammalian cells selected from CHO cells, Hek293 cells or COS cells. According to further particular embodiments, the mammalian cells are selected from CHO cells and Hek293 cells.

While the variety of host cells which can be engineered towards a GlycoDelete background described herein before can be particularly useful to produce the specific glycans present on the polypeptide of the invention, it should be kept in mind that also combined in vivo and in vitro approaches are possible to obtain the desired glycan structures as claimed in the composition of the invention. Indeed, polypeptides of the invention which have been produced in wild type eukaryotic hosts can be purified, the glycan structures can be trimmed by suitable endoglucosaminidases or exo-glycosidases and thereafter can be re-built by the in vitro use of specific glycosyltransferases (e.g. galactosyltransferases and the like). Also, GlycoDelete-engineered lower eukaryotic cells (e.g. yeast cells) which produce polypeptides having only GlcNAc N-glycans on the produced glycoproteins can be further modified in vitro with a beta-1,4-galactosyltransferase to comprise LacNAc as N-glycan structures.

The recombinant glycoproteins produced by the cells described herein typically should be easily recovered. This will particularly be achieved by secretion of the glycoprotein. The nature of the secretion signal typically depends on the type of eukaryotic cells used. As long as the secretion signal is functional in the cell type in which it is used (i.e. it results in secretion to the extracellular environment of the protein or peptide to which it is fused), this feature is not critical to the invention. Thus, secretion signals from other organisms may be used, as long as these signals lead to secretion in the eukaryotic cells used. Secretion signals are well known in the art and may be derived from—typically the N-terminus of—proteins that are secreted, or may be made synthetically (e.g. Tan et al., Protein engineering 2002, vol. 15, no4, pp. 337-345). Alternatively, they can be derived from genomic sequences using computational methods (Klee et al., BMC Bioinformatics 2005, 6:256). Also, bacterial secretion signals can be used. Further examples of signal peptides that can be used are described in WO2002/048187 (eukaryotic cells), Schaaf et al. (BMC Biotechnol. 2005; 5: 30) (moss cells), EP549062. Specific secretion signals used in yeast include e.g. α-factor secretory peptide, the PHO5 secretory peptide, and the BAR1 secretion signal.

The enzymes which are expressed in the (higher) eukaryotic cells of the invention may be operably linked to an ER or Golgi localization signal. Such signal directs the enzymes to the ER or Golgi, respectively, where it is retained. As the ER and Golgi apparatus are the intracellular locations where glycosylation of proteins takes place, targeting to these organelles ensures that the enzymes are directed to the correct intracellular position to modify the glycosylation of the glycoprotein. Several ER- and Golgi-residing enzymes are type II membrane proteins. These proteins have a common domain structure comprising a short cytoplasmic tail at the amino terminus, a hydrophobic transmembrane domain, a luminal stem and a C-terminal catalytic domain. Deletion studies as well as fusions to non-Golgi-residing proteins have identified the N-terminus, and in particular the transmembrane region, as containing the targeting information of many type II membrane proteins. Localization signals are well known in the art and may be derived from proteins that are normally localized in the ER or Golgi for their function. Moreover, localization sequences from one organism may function in other organisms. According to particular embodiments, the ER or Golgi localization signal is from a protein that is itself localized in the ER or Golgi when functionally active. Examples of such proteins include but are not limited to human β-galactoside-α-2, 6-sialyltransferase (ST6Gall) and the human ganglioside-GM$_2$-synthase. According to further embodiments, the localization sequence is derived from one of the following proteins: GL2-synthase, ganglioside-GM$_2$-synthase, and α-2,6-glycosyltransferase, in particular α-2,6-sialyltransferase, most particularly β-galactoside-α-2,6-sialyltransferase. Although, in addition to the glycoprotein, the endoglucosaminidase may also be secreted by the cell (using identical or similar secretion signals—i.e., the remarks on secretion signals for glycoproteins also apply for endoglucosaminidases), it can be a particular advantage that the endoglucosaminidase remains in the cell. This takes away the need for separation of the endoglucosaminidase and the glycoprotein which arises when both proteins are secreted. Most particularly, the endoglucosaminidase not only remains in the cell, but is also fully active. Its activity should be regulated spatiotemporally, in order to ensure that the desired hydrolysis takes place. To this end, the endoglucosaminidase may be operably linked to an ER or Golgi localization signal. Such signal directs the endoglucosaminidase to the ER or Golgi, respectively, where it is retained. As the ER and Golgi apparatus are the intracellular locations where glycosylation of proteins takes place, targeting to these organelles ensures that the endoglucosaminidase is in the correct intracellular position to modify the glycosylation of the glycoprotein.

Although secretion is particularly envisaged for easy recovery of glycoproteins, alternative options exist. The produced glycoproteins may for instance be deposited in inclusion bodies in the cell, or in membrane-bound organelles or in structures with similar functions. It should be noted that, particularly in cases where the protein is not secreted, it is possible that the protein is deposited in an inactive form. Thus, additional refolding or re-activating steps may be needed in order to obtain a physiologically relevant form of the glycoprotein.

Glycoprotein-Conjugates

In a particular embodiment the invention provides glycoprotein-conjugates. In a preferred embodiment the glycoproteins according to the invention are coupled to a specific moiety (a conjugated moiety as defined herein before) via the LacNAc N-glycan structures present on said glycoproteins. Such glycan specific coupling to a specific glycan moiety is referred to in the art as glycan-specific conjugation. Glycan structures with specific LacNAc terminal carbohydrates as herein described before present on the glycoproteins are used as a starting point for the coupling with a specific moiety.

In the present invention "a glycoprotein of the invention" is a glycoprotein comprising N-glycans consisting of LacNAc residues is present at more than 40%, more than 50%, more than 60%, more than 70%, more than 80% or even more than 90% of the total amount of N-glycans present on said glycoprotein.

Specific Moieties Which can be Used for Conjugation

A plethora of conjugated moieties exist in the art which can be used for coupling to the LacNAc N-glycan structure present on the glycoproteins of the invention. Conjugated moieties comprise for example a half-life extending moiety, a therapeutic agent, a detection unit, a targeting moiety or even a second (the same or different) glycoprotein. One or more conjugated moieties, which can also be different from each other, can be linked to the glycoprotein of the invention. Even one conjugated moiety can have more than one function, i.e. a half-life extending moiety can at the same time be useful as a targeting moiety.

i) Half-Life Extending Moieties

Various half-life extending moieties are envisaged herein. Non-limiting and in brief, reference is made to the half-life extension strategies described in Kontermann, R. E., Expert Opin Biol Ther. 16(7), 2016 or van Witteloostuijn, S. B., ChemMedChem. 11(22), 2016. In particular, a variety of half-life extension techniques relying on covalent chemical modification have been developed. These methods include PEGylation, fusion to unstructured polypeptide-based PEG mimetics, employment of polysialylation (e.g. enzymatic use of polysialyltransferase enzymes), biotin-coupling, polyoxazoline-coupling, conjugation with large polysaccharides, lipidation, fusion to albumin or the Fc domain of IgG, and derivatization with bio-orthogonal moieties that direct self-assembly.

ii) Therapeutic Moieties

In certain embodiments the conjugated moiety comprises various therapeutic agents including i.e. anti-inflammatory, anticancer, cytotoxic, anti-infective (e.g., anti-fungal, anti-bacterial, anti-parasitic, anti-viral, etc.), and anesthetic therapeutic agents. In specific embodiments the conjugated moiety is an enzyme capable of converting a prodrug which is converted into a toxic drug. A toxic agent (e.g. a toxin, a cytotoxic drug, a radionuclide) can also be suitable for therapeutic purposes and is particularly useful in cancer therapy. Hence, a specific example of a glycoprotein-conjugate is an antibody-drug-conjugate (ADC). In principal, every agent suitable for therapeutic purposes is envisaged herein. Therapeutic agents as described are typically small molecules or biologics, but therapeutic agents can also be of another origin what should be clear to the skilled person and the invention should not be limited thereto.

iii) Detection Moieties

In certain embodiments the conjugated moiety comprises a detection moiety. The term "detection moiety" or "detectable label" refers to any unit possessing a property or function which can be used for detection purposes, i.e. those selected from the group comprising a chromophore unit, fluorescent unit, phosphorescent unit, luminescent unit, light absorbing unit, radioactive unit, and transition metal isotope mass tag unit. Without being limiting, the detection moiety can be a small or a large molecule as should be clear to the skilled person.

Suitable fluorescent units are those known from the art of immunofluorescence technologies, e.g., flow cytometry or fluorescence microscopy. In these embodiments of the invention, the conjugate comprising the detection unit is detected by exciting the detection unit and detecting the resulting emission (photoluminescence). In this embodiment, the detection unit is preferably a fluorescent unit.

Useful fluorescent units might be protein-based, such as phycobiliproteins, polymeric, such as polyfluorenes, small organic molecule dyes, such as xanthenes, like fluorescein, or rhodamines, cyanines, oxazines, coumarins, acridines, oxadiazoles, pyrenes, pyrromethenes, or metallo-organic complexes, such as Ru, Eu, Pt complexes. Besides single molecule entities, clusters of fluorescent proteins or small organic molecule dyes, as well as nanoparticles, such as quantum dots, upconverting nanoparticles, gold nanoparticles, dyed polymer nanoparticles can also be used as fluorescent units.

Another group of photoluminescent detection units are phosphorescent units with time-delayed emission of light after excitation. Phosphorescent units include metallo-organic complexes, such as Pd, Pt, Tb, Eu complexes, or nanoparticles with incorporated phosphorescent pigments such as lanthanide doped $SrAl2O4$.

In another embodiment of the invention the conjugate comprising the detection unit is detected without prior excitation by irradiation. In this embodiment the detection unit can be a radioactive label. They may be in the form of radioisotope labeling by exchanging non-radioactive isotopes for their radioactive counterparts, such as tritium, $^{32}P$, $^{35}S$ or $^{14}C$, or introducing covalently bound labels, such as $^{125}I$, which is bound to tyrosine, $^{18}F$ within fluorodeoxyglucose, or metallo-organic complexes, i.e. $^{99}Tc$-DTPA.

In another embodiment the detection unit is capable of causing chemiluminescence, i.e. horseradish peroxidase label in the presence of luminol.

In another embodiment of the invention the conjugate comprising the detection unit is not detected by radiation emission, but by absorption of UV, visible light, or NIR radiation. Suitable light-absorbing detection moieties are light absorbing dyes without fluorescence emission, such as small organic molecule quencher dyes like N-aryl rhodamines, azo dyes, and stilbenes.

In another embodiment, the light-absorbing detection unit can be irradiated by pulsed laser light, generating a photoacoustic signal.

In another embodiment of the invention the conjugate comprising the detection unit is detected by mass spectrometric detection of a transition metal isotope. Transition metal isotope mass tag labels might be introduced as covalently bound metallo-organic complexes or nanoparticle component. Known in the art are isotope tags of lanthanides and adjacent late transition elements.

iv) Targeting Moiety

In certain embodiments, the conjugated moiety comprises a targeting moiety. As used herein, the term "targeting moiety" refers to a conjugated moiety that binds to a target molecule. Small molecules or biologics can both be employed as a targeting moiety. Targeting moieties can comprise, without limitation, proteins, nucleotide sequences, lipids, other carbohydrates (e.g. specific glycans), and combinations thereof (e.g., glycoproteins, glycopeptides, and glycolipids). Any moiety which is able to bind to a target can be employed as a targeting moiety according to the invention.

Linkers Useful in the Glycoprotein-Conjugates

In certain embodiments the glycoprotein-conjugates comprise a linker between the LacNAc N-glycan and the targeting moiety. Certain linkers are more useful than others and the use of a specific linker will depend on the application. For example oximes and hydrazones, in particular derived from aliphatic aldehydes, show less stability over time in water or at lower pH. Aromatically stabilized structures can be more useful to stably link a glycan to a conjugated moiety. Such stabilized linkers are also within the scope of the present application, as they can limit adverse effects due to premature release of the conjugated moiety, particularly when the conjugated moiety is a toxic substance intended for killing of a tumor cell. Of particular interest are BICYCLO[6.1.0]NON-4-YNE REAGENTS as well as aromatically stabilized triazole linkers and sulfamide linkers. It is within common technical knowledge that increased stability of a conjugate can also result from reduced aggregation tendency of any of the moieties comprised within said conjugate. For the production of glycoprotein-conjugates with increased stability the reader is non-exclusively referred to WO2013036748, WO2014065661, WO2015057064 and WO2016053107 as well as to other patent applications filed by Synaffix B. V. explicitly mentioned herein.

In general, various linkers known in the art can be used to link the glycoprotein and the conjugated moiety according to the invention. As should be clear, cleavable and non-cleavable linkers can be employed to achieve the desired release profile. In general, the optimal combination of linker and conjugation chemistry must be uniquely tailored to correlate each unique facet: the IVD, the conjugated moiety, and the profile of the disease to be treated. For reviews on antibody-drug conjugates and linkers used herein see for example Jessica R. McCombs and Shawn C. Owen, AAPS J. 17(2), 2015 and Lu, J. et al., Int J Mol Sci. 17(4), 2016 as well as a recent review by Pillow, T.H., Pharm Pat Anal. 6(1), 2017 describing a novel quaternary ammonium salt linker useful in conjugates for the treatment of cancer and infectious diseases.

Still other suitable spacers or linkers will be clear to the skilled person, and may generally be any linker or spacer used in the art. In specific aspects the linkers or spacers are suitable for use in applications which are intended for pharmaceutical use. For example, a linker between the glycan and the moiety in the glycoprotein-conjugate may in certain aspects also be a suitable amino acid sequence, and in particular amino acid sequences of between 1 and 50, or more specifically, between 1 and 30 amino acid residues. Some examples of such amino acid sequences include Gly-Ser (GS) linkers, such as for example (GS)n or (GGGSS)n or (GSS)n, as described in WO 99/42077 and the $(G4S)_3$, $GS_{30}$, $GS_{15}$, $GS_9$ and $GS_7$ linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Still other suitable linkers generally comprise organic compounds or polymers, in particular those suitable for use in polypeptides for pharmaceutical use. For instance, poly(ethyleneglycol) moieties have been used to link antibody domains, see for example WO 04/081026. It is encompassed within the scope of the invention that the length, the degree of flexibility and/or other properties of the linker may have some influence on the properties of the final glycoprotein-conjugate of the invention, including but not limited to the affinity, specificity or avidity for a specific target. Based on the disclosure herein, the skilled person will be able to determine the optimal linker for use in a specific glycoprotein of the invention, optionally after some limited routine experiments. For example, in multivalent glycoproteins of the invention that comprise building blocks, directed against a first and second target, the length and flexibility of the linker is preferably such that it allows each building block to bind to its cognate target. Again, based on the disclosure herein, the skilled person will be able to determine the optimal linker for use in a specific glycoprotein of the invention, optionally after some limited routine experiments. Finally, when two or more linkers are used in the glycoprotein of the invention, these linkers may be the same or different. Again, based on the disclosure herein, the skilled person will be able to determine the optimal linkers for use in a specific polypeptide of the invention, optionally after some limited routine experiments. In certain specific embodiments it is desirable to produce glycoprotein-conjugates with longer linkers including for example carbohydrates, which can provide the glycoprotein-conjugate with higher hydrophilicity and accordingly improved water-solubility. Glycoprotein-conjugates comprising linkers with more carbohydrates are thus also within the scope of the present application. Also, linkers modified with PEG or consisting of PEG can be useful to increase the hydrophilic properties of a glycoprotein-conjugate.

Coupling Methods to Link Specific Moieties to a Glycoprotein of the Invention

In yet another embodiment the invention provides methods to produce a glycoprotein-conjugate of the invention. Generally, such methods start by introducing an expression vector comprising a nucleotide sequence encoding a glycoprotein according to the invention in a suitable cell of choice, followed by expressing the glycoprotein for some time, purifying the glycoprotein and linking of a specific conjugated moiety to the purified glycoprotein. The coupling method itself is generally carried out in vitro.

Several possibilities exist in the art to link a specific conjugated moiety to a glycoprotein of the invention. Generally spoken there are chemical, enzymatic and combined chemo-enzymatic conjugation strategies to carry out the coupling reaction.

According to a particular embodiment, the method to produce a glycoprotein-conjugate comprises the steps of
oxidizing the vicinal diol or diols present in LacNAc N-glycans of a glycoprotein of the invention
reacting the obtained free aldehyde groups with hydroxylamine-containing molecules.

For oxidation, sodium periodate or several other comparable reagents known in the art can be used. In a specific embodiment the diol to be oxidized originates from a LacNAc disaccharide present on the glycoprotein of the invention. Oximes are formed by subsequent reaction of the resulting free aldehyde groups with aminooxy-containing molecules, commonly described as LacNAc oxidation-oxime ligation chemistry. Well-known in the art is the use of catalysts like para-phenylenediamine, 2-aminophenols or 2-(aminomethypenzimidazoles. Oxime and hydrazine conjugation are a promising alternative to click-chemistry, a more complex biorthogonal modification strategy. Under reductive amination conditions, the dialdehyde can be reacted with amines, which results in stable oxazepine derivatives.

According to another particular embodiment, said method to produce an glycoprotein-conjugate optionally comprises the steps of
oxidizing the C6 hydroxyl group of a Gal residue in the terminal LacNAc N-glycan present on a glycoprotein of the invention
reacting the free aldehyde group with hydroxylamine-containing molecules.

For oxidation, the enzyme Galactose Oxidase (GAO) can be used. Employing the above mentioned steps typically oxime bonds are formed, optionally in the presence of a catalase, all of this is well-known in the art.

To modulate or to particularly increase stability of oximes and hydrazones, the use of linkers as described before is particularly envisaged herein.

The use of linkers to modulate the stability of glycoprotein-conjugates as described before is particularly envisaged herein.

Several specific methods are specified in detail in the examples section further below.

Applications of Glycoprotein-Conjugates of the Invention

In a particular embodiment, a glycoprotein-conjugate of the invention is used to modulate the circulation half-life or to increase the glycoprotein stability, for selective targeting, to modulate immunogenicity of the glycoprotein-conjugate or for detection purposes.

In yet another embodiment the glycoprotein-conjugates of the invention are used as a medicament.

In yet another embodiment the glycoprotein of the invention (not conjugated with any moiety) of the invention is used as a medicament.

With the wording "to modulate circulation half-life" it is meant that the half-life of the polypeptide (e.g. glycoprotein-conjugate) can be either increased or decreased. For some applications, it can be useful that the glycoprotein-conjugate of the invention remains in the bloodstream for a shorter time than polypeptides or conjugates lacking the specific properties of polypeptides or glycoprotein-conjugates as claimed. Often, prolonged half-life is aimed as many therapeutic molecules are smaller than the renal filtration threshold and are rapidly lost from the circulation thereby limiting their therapeutic potential. As a non-limiting example, albumin or other half-life extending moieties as referred to above can be used in a variety of ways known to the skilled practitioner to increase the circulatory half-life of such molecules.

With "selective targeting" it is meant that glycoprotein-conjugates of the invention can be useful to achieve an exclusive effect on the target of interest. An example of this is conventional chemotherapy where selective targeting of cancer cells without interacting with the normal body cells often fails. As a consequence thereof, serious side effects are caused including organ damage resulting in impaired treatment with lower dose and ultimately low survival rates. Glycoprotein-conjugates of the invention, optionally comprising a targeting moiety, can be useful to overcome the disadvantages of conventional approaches not limited to cancer therapy.

Glycoprotein-conjugates of the invention are also provided for detection purposes, particularly when comprising a detection unit as explained before. Particularly, glycoprotein-conjugates of the invention are more prone for detection purposes than glycoproteins lacking the specific properties of the claimed glycoprotein-conjugates.

Thus, in a particular embodiment the glycoprotein-conjugates of the invention can also be used for diagnostic purposes.

In yet another embodiment the invention provides kits comprising glycoproteins of the present invention.

In yet another embodiment the invention provides kits comprising glycoprotein-conjugates of the present invention.

In another embodiment, a pharmaceutical composition is provided comprising a glycoprotein-conjugate as described before.

Therefore, the present invention includes pharmaceutical compositions that are comprised of a pharmaceutically acceptable carrier and a pharmaceutically effective amount of glycoprotein-conjugates of the invention and a pharmaceutically acceptable carrier. A pharmaceutically acceptable carrier is preferably a carrier that is relatively non-toxic and innocuous to a patient at concentrations consistent with effective activity of the active ingredient so that any side effects associated with the carrier do not vitiate the beneficial effects of the active ingredient. A pharmaceutically effective amount of polypeptides of the invention and a pharmaceutically acceptable carrier is preferably that amount which produces a result or exerts an influence on the particular condition being treated. The polypeptides of the invention and a pharmaceutically acceptable carrier can be administered with pharmaceutically acceptable carriers well known in the art using any effective conventional dosage form, including immediate, slow and timed-release preparations, and can be administered by any suitable route such as any of those commonly known to those of ordinary skill in the art. For therapy, the pharmaceutical composition of the invention can be administered to any patient in accordance with standard techniques. The administration can be by any appropriate mode, including orally, parenterally, topically, nasally, ophthalmologically, intrathecally, intracerebroventricularly, sublingually, rectally, vaginally, and the like. Still other techniques of formulation as nanotechnology and aerosol and inhalant are also within the scope of this invention. The dosage and frequency of administration will depend on the age, sex and condition of the patient, concurrent administration of other drugs, counter-indications and other parameters to be considered by the clinician.

The pharmaceutical composition of this invention can be lyophilized for storage and reconstituted in a suitable carrier prior to use.

When prepared as lyophilization or liquid, physiologically acceptable carrier, excipient, stabilizer need to be added into the pharmaceutical composition of the invention (Remington's Pharmaceutical Sciences 22th edition, Ed. Allen, Loyd V, Jr. (2012). The dosage and concentration of the carrier, excipient and stabilizer should be safe to the subject (human, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as TWEEN™, PLURONICS™ or PEG and the like.

The preparation containing pharmaceutical composition of this invention should be sterilized before injection. This procedure can be done using sterile filtration membranes before or after lyophilization and reconstitution.

The pharmaceutical composition is usually filled in a container with sterile access port, such as an i.v. solution bottle with a cork. The cork can be penetrated by hypodermic needle.

Therefore, the present invention includes pharmaceutical compositions that are comprised of a pharmaceutically acceptable carrier and a pharmaceutically effective amount of polypeptides, nucleotide sequences and glycoprotein-conjugates of the invention and a pharmaceutically acceptable carrier. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of polypeptides, nucleotide sequences and conjugates of the invention and a pharmaceutically acceptable carrier is preferably that amount which produces a result or exerts an influence on the particular condition being treated. The polypeptides, nucleotide sequences and conjugates of the invention and a pharmaceutically acceptable carrier can be administered with pharmaceutically acceptable carriers well known in the art using any effective conventional dosage form, including immediate, slow and timed release preparations, and can be administered by any suitable route such as any of those commonly known to those of ordinary skill in the art. For therapy, the pharmaceutical composition of the invention can be administered to any patient in accordance with standard techniques. The administration can be by any appropriate mode, including orally, parenterally, topically, nasally, ophthalmologically, intrathecally, intracerebroventricularly, sublingually, rectally, vaginally, and the like. Still other techniques of formulation as nanotechnology and aerosol and inhalant are also within the scope of this invention. The dosage and frequency of administration will depend on the age, sex and condition of the patient, concurrent administration of other drugs, counter-indications and other parameters to be taken into account by the clinician.

The pharmaceutical composition of this invention can be lyophilized for storage and reconstituted in a suitable carrier prior to use.

When prepared as lyophilization or liquid, physiologically acceptable carrier, excipient, stabilizer need to be added into the pharmaceutical composition of the invention (Remington's Pharmaceutical Sciences 22th edition, Ed. Allen, Loyd V, Jr. (2012). The dosage and concentration of the carrier, excipient and stabilizer should be safe to the subject (human, mice and other mammals), including buffers such as phosphate, citrate, and other organic acid; antioxidant such as vitamin C, small polypeptide, protein such as serum albumin, gelatin or immunoglobulin; hydrophilic polymer such as PVP, amino acid such as amino acetate, glutamate, asparagine, arginine, lysine; glycose, disaccharide, and other carbohydrate such as glucose, mannose or dextrin, chelate agent such as EDTA, sugar alcohols such as mannitol, sorbitol; counterions such as Na+, and/or surfactant such as TWEEN™, PLURONICS™ or PEG and the like.

The preparation containing pharmaceutical composition of this invention should be sterilized before injection. This procedure can be done using sterile filtration membranes before or after lyophilization and reconstitution.

The pharmaceutical composition is usually filled in a container with sterile access port, such as an i.v. solution bottle with a cork. The cork can be penetrated by hypodermic needle.

It is to be understood that although particular embodiments, specific configurations as well as materials and/or molecules, have been discussed herein for nucleotide sequences, cells, polypeptides, conjugates and methods according to the present invention, various changes or modifications in form and detail may be made without departing from the scope and spirit of this invention. The following examples are provided to better illustrate particular embodiments, and they should not be considered limiting the application. The application is limited only by the claims.

Examples

1. Optimizinq LacNAc N-Glycan Formation in Higher Eukaryotic Cells with a GlycoDelete Background Previously we (see Meuris L. et al (2014) Nat. Biotechn. 32(5) 485) disclosed that recombinant glycoproteins produced in the mammalian HEK293 cells having a GlycoDelete background carry a mixture of N-glycans consisting of GlcNAc, N-glycans consisting of LacNAc, and N-glycans consisting of sialyl-LacNAc of which the LacNAc- and sialyl-LacNAc-N-glycans constitute 90% of the N-glycans. Quantification of the relative glycopeptide peak areas of samples before and after sialidase treatment allowed us to establish that 19% of the anti-CD20 carries the sialylated trisaccharide and 72% carries the Gal-GlcNAc (LacNAc) disaccharide.

In the present example, we investigated whether knock out of the UDP-GlcNAc-2-Epimerase/ManNAc Kinase (GNE) gene, which is essential for CMP-sialic acid synthesis, would lead to more homogeneous forms of N-glycans and to a higher percentage of LacNAc N-glycans on a recombinant glycoprotein. The GNE knockout was generated using targeted CRISPR/Cas9 mutagenesis, according to established methods in the art. In a next step, we also consider the overexpression of exogenously introduced human β-1,4-Galactosyltransferase (GalT) in the mammalian host cell to further increase the LacNAc levels of the N-glycans. In addition, we also consider the overexpression of exogenously introduced UDP-Glc-4-epimerase and the overexpression of UDP-galactose transporter. As a first proof-of-concept, we recombinantly expressed the glycoprotein obinutuzumab, a CD20-specific monoclonal antibody commercialized under the brand name Gazyva®. LacNAc N-glycosylation efficiency in the engineered cell lines was evaluated via LC-ESI-MS analysis of the reduced heavy chains derived from obinutuzumab produced in the respective cell lines.

TABLE 1

The relative abundance of different glycoforms of obinutuzumab produced in GlycoDelete cells in which the GNE gene is knocked out.

| Glycan | % abundance |
|---|---|
| GlcNAc | 7.9% |
| LacNAc | 92.1% |
| LacNAc-Sia | 0% |

As a second proof-of-concept, we recombinantly expressed a glyco-engineered GFP-binding nanobody (abbreviated as GBP_R86N) in these higher eukaryotic cells (for details about this nanobody see example 2). LacNAc N-glycosylation efficiency in the engineered cell lines was evaluated via LC-ESI-MS analysis of the intact protein. 96% of the glycosylated GBP had an N-glycan consisting of a LacNAc carbohydrate chain and no sialic acid containing N-glycans could be detected.

2. Optimizing LacNAc N-Glycan Formation in Lower Eukaryotic Cells with a GlycoDelete Background Recombinant glycoproteins expressed in the Pichia pastoris GlycoDelete strain are homogeneously modified with N-glycans consisting of single GlcNAc residues N-glycans (see for example Claes, K. et al. (2016) ACS Synth Biol. 5(10)). In this experiment we investigated whether the exogenous introduction of the human beta-(1,4) galactosyltransferase would lead to an optimal formation of homogeneous LacNAc structures on recombinant glycoproteins expressed in this P. pastoris strain. A glyco-engineered GFP-binding nanobody (GBP_R86N) was selected as a benchmark protein. This protein was obtained by introducing a point mutation (mutation R86N (aHo numbering) to introduce an artificial N-glycosylation site) in the wild type GFP-binding nanobody (GBP; published by Kubala, M. H. et al (2010) Protein Sci. 19(12)). The amino acid sequence of the wild type GBP nanobody is depicted in SEQ ID NO: 1. In SEQ ID NO: 1 the CDR1, CDR2 and CDR3 regions are underlined.

```
SEQ ID NO 1:
QVQLVESGGALVQPGGSLRLSCAASGFPVNRYSMRWYRQAPGKEREWVAG

MSSAGDRSSYEDSVKGRFTISRDDARNTVYLQMNSLKPEDTAVYYCNVNV

GFEYWGQGTQVTVSSHHHHHH (121 amino acids)
```

An expression vector was made wherein the coding sequence of the GBP_R86N nanobody (with artificially introduced N-glycosylation acceptor site) is operably linked to the AOX1 promoter (a methanol inducible promoter) of Pichia pastoris. The resulting expression vector was introduced in a Pichia pastoris Glycodelete strain that stably expresses human beta-(1-4)-galactosyltransferase.

The transformed Pichia pastoris strain was first grown for 48h at 28° C. in medium containing glycerol as the sole carbon source; subsequently, protein expression was induced by replacing glycerol with methanol. After another 48 hours at 28° C., the growth medium (supernatant) of the recombinant culture was collected.

100 mM reduced glutathion and 2 mM MgCl2 were added to the supernatant, and the pH of the culture broth was set to pH 7.5 with 1M NaOH. Any precipitation was removed using a 0.22 μm bottle top vacuum filter (Millipore). The filtered GBP formats were loaded on a 5 ml HisTrap HP IMAC-column. The column was washed with 10 column volumes of buffer A (20 mM Imidazole, 500 mM NaCl, 20 mM NaH2PO4/Na2HPO4 pH 7.5) before eluting with a linear gradient (10CV) against buffer B (500 mM Imidazole, 500 mM NaCl, 20 mM NaH2PO4/Na2HPO4 pH 7.5). The GBP-containing fractions were pooled and polished over a Superdex 75 prep grade (16/600) column equilibrated with 25 mM HEPES, 150 mM NaCl, pH 7.4.

LacNAc glycosylation of the GBP_R86N protein was confirmed via mass spectrometry analysis. GBP_R86N nanobody was either treated with β-1,4-galactosidase (Streptococcus pneumoniae) or mock treated. Subsequently, the samples were diluted to 10 pmole per μl in ultrapure water and analyzed on a Q Executive BioPharma mass spectrometer (Thermo Scientific) with an in line desalting step. Deconvolution and data processing was performed with Thermo Xcalibur Qual Browser.

In the mock treated sample (FIGS. 3A), we detected peaks that correspond to the molecular weight of non-glycosylated GBP_R86N ("GBP"), single GlcNAc-modified GBP_R86N ("GBP-GlcNAc") and GBP_R86N modified with a GlcNAc-Gal glycan (GBP-GlcNAcGal). In the galactosidase treated sample (FIGS. 3B), we could no longer observe the peak corresponding to the GBP_R86N carrying the LacNAc glycan (GBP-GlcNAcGal).

Although *P. pastoris* can form endogenous UDP-Gal, in a next step we also evaluate whether the introduction of the human UDP-Glc-4-epimerase (GalE; converts UDP-Glc to UDP-Gal) gene further increases the efficiency of LacNAc formation in *Pichia pastoris*. The effects of the engineering steps on the efficiency of LacNAc N-glycosylation by the resulting recombinant *Pichia pastoris* strains is analysed using LC-ESI-MS of the tryptic glycopeptides derived from the glycoproteins produced in these cells.

3. Optimizing LacNAc N-Glycan Formation in Higher Eukaryotic Cells with a GlycoDoubleDelete Background In HEK293s cells having a GlycoDoubleDelete background the GalE gene is knocked out. As a result of this, UDP-glucose and UDP-GlcNAc can no longer be epimerized to UDP-galactose and UDP-GalNAc. However, mammalian cells have evolved a salvage pathway to synthesize these high energy sugar forms. Both galactose and GalNAc can be transported from the medium into the cell and can be transformed to their respective high energy forms. When we produced recombinant hGM-CSF in HEK293s GlycoDoubleDelete cells that grow in galactose- and GalNAc-free medium, we were unable to detect any galactosylated N-glycans or mucin-type O-glycans on mass spec. In contrast, Western blot analysis of hGM-CSF produced in medium supplemented with galactose clearly showed a higher MW band compared to the protein produced under Gal/GalNAc-free conditions, indicating the presence of LacNAc and LacNAc-Sia GlycoDelete type N-glycans on the protein. Similar results were obtained when we produced an antibody (obinuzutumab) in galactose-supplemented HEK293s GlycoDoubleDelete cells. Glycoprofiling of the Fc region using ESI-MS showed that approximately 30% of the Fc tails carry a Neu5Ac-α-2,3-Gal-β-1,4-GlcNAc trisaccharide and 50% a Gal-β-1,4-GlcNAc disaccharide, which is in the same range as HEK293sGlycoDelete-produced antibody. The above data indicate that the salvage pathway to use galactose from the medium for glycosylation is very efficient in HEK293 cells. By adding galactose to the medium of HEK293sGlycoDoubleDelete cells, proteins can be produced that carry LacNAc-Sia type N-glycans and no mucin-type O-glycans. If we additionally block the sialylation pathway in these cells by knocking out e.g. GNE, other enzymes in the CMP-sialic acid synthesis pathway, or specific sialyltransferases, the glycosylation pathway is limited to the production of LacNAc type N-glycans and still unable to synthesize mucin-type O-glycans. Consequently, these sialylation-deficient GlycoDoubleDelete cells can be used to produce proteins with predominantly LacNAc type N-glycans and no mucin-type O-glycans when grown in galactose-containing medium. An overview of the strategy is shown in FIG. 2.

4. Development of LacNAc Glycan-Specific Conjugation Methods

The data from the previous examples convincingly show that homogeneous forms of LacNAc N-glycans can be produced on glycoproteins expressed in suitable eukaryotic cells of the invention. These data pave the way for glycan-based conjugation strategies of glycoproteins. In the following examples we are using nanobodies with simple and homogeneous N-glycans introduced in an artificially engineered N-glycosylation site as outlined in Example 2 for the application of glycan-specific conjugation methods. The homogeneous LacNAc N-glycans provide for a bio-orthogonal handle on the protein that can be used for coupling to a wide variety of desired moieties—e.g. PEG chains, chelators, toxic drugs etc. Different glycan-based conjugation chemistries are evaluated/optimized, using commercially available biotinylated PEG. Basically in the art there exist two broad methods for conjugation: combined chemical and enzymatic conjugation methods as exemplified in example 5 and chemical conjugation as exemplified in example 6.

5. Chemo-Enzymatic Conjugation Strategies

In this example, we show how a nanobody with an artificially introduced N-glycan at position 86 (Aho numbering) can be specifically modified with PEG-biotin on the glycan. The nanobody is first recombinantly expressed in a HEK293 GlycoDelete cell, a HEK293 GlycoDoubleDelete cell, or a *Pichia*-GlycoDelete cell that has been engineered to produce homogeneous LacNAc-type N-glycosylation (See examples 1, 2 and 3). Glycoproteins comprising homogeneous forms of LacNAc N-glycans yield more homogeneous and pure conjugated products in glycan-based conjugation (in contrast to the more heterogeneous situation for wild type glycans).

In a first strategy, we use the enzyme Galactose Oxidase (GAO) to oxidize the C6 hydroxyl group of the Gal residue in the artificially introduced LacNAc glycan on the nanobody of interest. This enzymatic oxidation creates a free aldehyde group, which can be linked to a molecule of interest via oxime ligation, hydrazone ligation or reductive amination (Park, A. et al., *Endocrinology* 154, 2013). The free aldehyde can readily react with aminooxy-containing molecules to form oximes, which are immediately stable in water. Alternatively, the free aldehydes can be reacted with hydrazine-containing molecules to form a stable hydrazone linkage, or they can be linked to amine-containing molecules via reductive amination. The LacNAc glycans conjugated in this manner retain an intact GlcNAc residue directly linked to the protein asparagine, which is favourable in terms of conjugate degradability in the lysosome. The schematic outline of GAO-based LacNAc oxidation, coupled with subsequent oxime ligation, is illustrated in FIG. 4. Briefly, GBP carrying an R86N mutation was recombinantly produced in *Pichia* GlycoDelete cells which co-express a galactosyltransferase. Proteins were purified, yielding a mixture of non-glycosylated protein and protein carrying GlcNAc or LacNAc. The purified protein derived from *Pichia*-GlycoDelete with galactosyltransferase co-expression was then oxidized with GAO (or mock-treated) and linked to a short biotinylated and aminooxy-modified PEG chain in a one-pot reaction. Mass spec analysis showed that the PEG chain was selectively linked to LacNAc-carrying GBP (FIG. 6).

In an alternative chemo-enzymatic strategy, we can use the enzyme hST6Gal1 (Wu, Z. L., Carbohydrate Research 412, 2015) to conjugate an azide-modified form of Sia (AzSia) to the LacNAc N-glycan present on our nanobody of interest. Via the azide function, the introduced AzSia on the nanobody can homogeneously and site-specifically be functionalized with a PEG chain or another molecule of interest employing click chemistry (e.g. copper-free azide-alkyne cycloaddition reaction). The schematic outline is illustrated in FIG. 5.

Briefly, GBP carrying an R86N mutation was recombinantly produced in *Pichia* GlycoDelete cells which co-express a galactosyltransferase. Proteins were purified, yielding a mixture of non-glycosylated protein and protein carrying GlcNAc or LacNAc. The purified protein derived from *Pichia*-GlycoDelete with galactosyltransferase co-expression was then incubated with CMP-Azido-Sialic Acid and recombinant hST6Gal1 enzyme to add an AzSia residue to the LacNAc chain, and subsequently subjected to a click reaction with a short biotinylated and DBCO-modified PEG chain. Mass spec analysis showed that the PEG chain was selectively linked to LacNAc-carrying GBP that was modified with AzSia (FIG. 7).

cans on which periodate oxidation yields pure products (in contrast to the situation of wild type glycans). The LacNAc type glycans (GlcNAc-Gal) contain a single vicinal 'cis' diol in the galactose residue (at the C3 and C4 ring positions) which can be oxidized. Periodate oxidation of the vicinal diol present in the glycan creates free aldehyde groups, which can be linked to a molecule of interest via oxime ligation, hydrazone ligation or reductive amination. The schematic outline of LacNAc-based periodate oxidation, coupled with subsequent oxime ligation, is illustrated in FIG. 1.

```
                         SEQUENCE LISTING

<160> NUMBER OF SEQ ID NOS: 2

<210> SEQ ID NO 1
<211> LENGTH: 121
<212> TYPE: PRT
<213> ORGANISM: Lama glama

<400> SEQUENCE: 1

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser His His His His His His
        115                 120

<210> SEQ ID NO 2
<211> LENGTH: 5
<212> TYPE: PRT
<213> ORGANISM: Artificial Sequence
<220> FEATURE:
<223> OTHER INFORMATION: Linker

<400> SEQUENCE: 2

Gly Gly Gly Ser Ser
1               5
```

Azide-modified LacNAc glycans may also be obtained by feeding azide-modified monosaccharide precursors (Gal-NAz) to the GlycoDelete cells producing the protein of interest; this allows subsequent site-specific functionalization via click chemistry.

6. Chemical Conjugation Strategies

An alternative glycan-based conjugation strategy makes use of sodium periodate. Vicinal diol(s) in glycans are oxidized by sodium periodate (NaIO$_4$). Early versions of this chemistry have been in use for decades, e.g. to generate fluorescently labeled antibodies. Glyco-engineered nanobodies obtained via the GlycoDelete technology carry gly-

The invention claimed is:

1. A mammalian cell comprising:
   a first exogenous nucleic acid sequence encoding an endoglucosaminidase enzyme wherein the endoglucosaminidase enzyme is operably linked to a secretion signal or the endoglucosaminidase is linked to an ER or Golgi localization signal, and
   a second exogenous nucleic acid sequence encoding a glycoprotein,
   wherein the mammalian cell is deficient in at least one of the following enzymes: UDP-N-acetylglucosamine-2-epimerase/N-acetylmannosamine kinase (GNE), N-acetylneuraminate-9-phosphate synthase, CMP-sialic acid synthase, CMP-sialic acid transporter, and sialyltransferase;

wherein the mammalian cell produces no detectable N-glycans comprising sialic acid residues; and wherein the N-glycans on the glycoprotein consist of more than 90% LacNAc residues.

2. The mammalian cell of claim 1, wherein the mammalian cell further comprises a third exogenous nucleic acid sequence encoding a beta-1,4-galactosyltransferase and wherein the beta-1,4-galactosyltransferase is operably linked to an ER or Golgi localization signal.

3. A method of producing a glycoprotein, the method comprising:

producing a glycoprotein from the mammalian cell of claim 1.

* * * * *